US 9,192,320 B2

(12) United States Patent
Rahmer et al.

(10) Patent No.: US 9,192,320 B2
(45) Date of Patent: Nov. 24, 2015

(54) APPARATUS AND METHOD FOR INFLUENCING AND/OR DETECTING MAGNETIC PARTICLES IN A FIELD OF VIEW

(75) Inventors: Jurgen Erwin Rahmer, Hamburg (DE); Bernhard Gleich, Hamburg (DE); Jurgen Weizenecker, Stutensee (DE)

(73) Assignee: Koninklijke Philips N.V., Eindhoven (NL)

( * ) Notice: Subject to any disclaimer, the term of this patent is extended or adjusted under 35 U.S.C. 154(b) by 431 days.

(21) Appl. No.: 13/389,900

(22) PCT Filed: Aug. 16, 2010

(86) PCT No.: PCT/IB2010/053684
§ 371 (c)(1),
(2), (4) Date: Feb. 10, 2012

(87) PCT Pub. No.: WO2011/030247
PCT Pub. Date: Mar. 17, 2011

(65) Prior Publication Data
US 2012/0153948 A1   Jun. 21, 2012

(30) Foreign Application Priority Data
Sep. 11, 2009   (EP) .................................. 09170082

(51) Int. Cl.
   *G01R 33/44*   (2006.01)
   *A61B 5/05*    (2006.01)

(52) U.S. Cl.
   CPC ................. *A61B 5/05* (2013.01); *A61B 5/0515* (2013.01)

(58) Field of Classification Search
   CPC .............................. A61B 5/0515; A61B 5/05
   USPC .......... 600/407, 409, 420, 422–425; 324/204, 324/228, 307, 318; 607/105; 73/53.01; 702/57
   See application file for complete search history.

(56) References Cited

U.S. PATENT DOCUMENTS

2006/0189868 A1* 8/2006 Gleich et al. .................. 600/437
2008/0204009 A1  8/2008 Gleich et al.

(Continued)

FOREIGN PATENT DOCUMENTS

DE   10151778 A1   5/2003
EP    1304542 A2   4/2003

(Continued)

OTHER PUBLICATIONS

Rahmer Jurgen et al: "Signal encoding in magnetic particle imaging: properties of the system function", BMC Medical Imaging, Biomed Central, London, GB, vol. 9, No. 1 Apr. 1, 2009, p. 4.

(Continued)

*Primary Examiner* — Long V Le
*Assistant Examiner* — Colin T Sakamoto

(57) ABSTRACT

The present invention relates to an apparatus (100) for influencing and/or detecting magnetic particles in a field of view (28), wherein the field of view (28) comprises at least one sub field of interest covering at least a portion of an object of interest containing magnetic particles. The apparatus (100) applying the known principle of Magnetic Particle Imaging (MPI) comprises selection means for generating a magnetic selection field (50) having the known field pattern showing a field free point (FFP), drive means for changing the position in space of the FFP by means of a magnetic drive field, receiving means for acquiring detection signals depending on the magnetization of the magnetic particles within the field of view (28), a control unit (150) for controlling a signal receiving unit (140) comprised in the receiving means for acquiring a set of high resolution detection signals and a set of low resolution detection signals, wherein the set of high resolution detection signals depends on the magnetization of at least one subfield of interest and the set of low resolution detection signals depends on the magnetization of at least one adjacent subfield being arranged adjacent to the at least one subfield of interest, and a reconstruction unit (152) for reconstructing a particle distribution quantity depending on the set of high resolution detection signals and the set of low resolution detection signals. The present invention further relates to a corresponding method as well as to a computer program.

15 Claims, 6 Drawing Sheets

(56) References Cited

U.S. PATENT DOCUMENTS

| | | | |
|---|---|---|---|
| 2009/0232410 A1* | 9/2009 | Dahnke et al. | 382/266 |
| 2010/0072984 A1* | 3/2010 | Gleich et al. | 324/204 |
| 2011/0089942 A1* | 4/2011 | Goodwill et al. | 324/301 |

FOREIGN PATENT DOCUMENTS

| | | |
|---|---|---|
| WO | 2004091386 A2 | 10/2004 |
| WO | 2004091390 A2 | 10/2004 |
| WO | 2004091394 A2 | 10/2004 |
| WO | 2004091395 A2 | 10/2004 |
| WO | 2004091396 A2 | 10/2004 |
| WO | 2004091397 A2 | 10/2004 |
| WO | 2004091398 A2 | 10/2004 |
| WO | 2004091408 A2 | 10/2004 |
| WO | 2006064405 A1 | 6/2006 |
| WO | 2009074952 A2 | 6/2009 |

OTHER PUBLICATIONS

Gleich B et al: "Tomographic imaging using the nonlinear response of magnetic particles", Nature, Nature Publishing Group, London, GB, vol. 435, No. 7046, Jun. 30, 2005, pp. 1214-1217.

* cited by examiner

APPARATUS AND METHOD FOR INFLUENCING AND/OR DETECTING MAGNETIC PARTICLES IN A FIELD OF VIEW

FIELD OF THE INVENTION

The present invention relates to an apparatus and a corresponding method for influencing and/or detecting magnetic particles in a field of view. Further, the present invention relates to a computer program for implementing said method on a computer and for controlling such an apparatus.

BACKGROUND OF THE INVENTION

"Magnetic Particle Imaging" (MPI) is an emerging medical imaging modality. The first versions of MPI were two-dimensional in that they produced two-dimensional images. Future versions will be three-dimensional (3D). A time-dependent, or 4D, image of a non-static object can be created by combining a temporal sequence of 3D images to a movie, provided the object does not significantly change during the data acquisition for a single 3D image.

MPI is a reconstructive imaging method, like Computed Tomography (CT) or Magnetic Resonance Imaging (MRI). Accordingly, a MP image of an object's volume of interest is generated in two steps. The first step, referred to as data acquisition, is performed using a MPI scanner. The MPI scanner has means to generate a static magnetic gradient field, called "selection field", which has a single field free point (FFP) at the isocenter of the scanner. In addition, the scanner has means to generate a time-dependent, spatially nearly homogeneous magnetic field. Actually, this field is obtained by superimposing a rapidly changing field with a small amplitude, called "drive field", and a slowly varying field with a large amplitude, called "focus field". By adding the time-dependent drive and focus fields to the static selection field, the FFP may be moved along a predetermined FFP trajectory throughout a volume of scanning surrounding the isocenter. The scanner also has an arrangement of one or more, e.g. three, receive coils and can record any voltages induced in these coils. For the data acquisition, the object to be imaged is placed in the scanner such that the object's volume of interest is enclosed by the scanner's field of view, which is a subset of the volume of scanning.

The object must contain magnetic nanoparticles; if the object is an animal or a patient, a contrast agent containing such particles is administered to the animal or patient prior to the scan. During the data acquisition, the MPI scanner steers the FFP along a deliberately chosen trajectory that traces out the volume of scanning, or at least the field of view. The magnetic nanoparticles within the object experience a changing magnetic field and respond by changing their magnetization. The changing magnetization of the nanoparticles induces a time dependent voltage in each of the receive coils. This voltage is sampled in a receiver associated with the receive coil. The samples output by the receivers are recorded and constitute the acquired data. The parameters that control the details of the data acquisition make up the scan protocol.

In the second step of the image generation, referred to as image reconstruction, the image is computed, or reconstructed, from the data acquired in the first step. The image is a discrete 3D array of data that represents a sampled approximation to the position-dependent concentration of the magnetic nanoparticles in the field of view. The reconstruction is generally performed by a computer, which executes a suitable computer program. Computer and computer program realize a reconstruction algorithm. The reconstruction algorithm is based on a mathematical model of the data acquisition. As with all reconstructive imaging methods, this model is an integral operator that acts on the acquired data; the reconstruction algorithm tries to undo, to the extent possible, the action of the model.

Such a MPI apparatus and method have the advantage that they can be used to examine arbitrary examination objects—e.g. human bodies—in a non-destructive manner and without causing any damage and with a high spatial resolution, both close to the surface and remote from the surface of the examination object. Such an arrangement and method are generally known and are first described in DE 101 51 778 A1 and in Gleich, B. and Weizenecker, J. (2005), "Tomographic imaging using the nonlinear response of magnetic particles" in nature, vol. 435, pp. 1214-1217. The arrangement and method for magnetic particle imaging (MPI) described in that publication take advantage of the non-linear magnetization curve of small magnetic particles.

As already explained, spatial encoding in MPI is based on the motion of a field free point or region over an object of interest. Thereby, the spectral response of the magnetic nanoparticles changes with distance to the FFP. High spectral components of said spectral response only occur in close vicinity to the FFP path or trajectory, whereas low spectral components are spatially rather delocalized. In certain situations problems may occur arising from delocalized low spectral components of the spectral response of the magnetic nanoparticles. For example in case of only encoding a sub-volume of a larger object or in case of completely encoding a larger object by splitting up the spatial encoding process. Splitting up the spatial encoding process means splitting up the large object into small sub-volumes, conducting encoding and reconstruction of a sub-volume image for each sub-volume separately and combining the sub-volume images for obtaining an overall image of the whole large object. In such situations signals from outside a specific sub-volume for which an encoding is conducted contribute to the low frequency components of the spectral response originated from those magnetic nanoparticles arranged in the specific sub-volume. Said signals from outside lead to a falsifications in the particle distribution quantity reconstructed for the specific sub-volume and therefore to artifacts in the sub-volume image reconstructed for the specific sub-volume. As the spectral response of the magnetic nanoparticles to the motion of the FFP is not completely localized, especially for low frequency components existing because of the encoding of the specific sub-volume, signals from outside the specific sub-volume are picked up.

The above-mentioned problems also may arise in case of leaving out sub-volumes of the field of view for speeding up the encoding process, wherein such sub-volumes are left out that cover areas which are not of interest to the operator of the MPI apparatus or MPI scanner. This approach is applied to situations at which in addition to the object of interest further objects are covered by the field of view. A concrete example for applying such an approach is the field of cardiac exam. With cardiac exam only subfields covering the region of the heart are encoded, while subfields covering for instance the liver are not encoded.

Because of the above described artifacts occurring in certain situations in reconstructed images existing MPI apparatuses and corresponding methods are still not optimal.

SUMMARY OF THE INVENTION

It is an object of the present invention to provide an apparatus and a corresponding method for influencing and/or detecting magnetic particles in a field of view by which the quality of reconstructed images is improved. Especially, artifacts in reconstructed images arising from low frequency components shall be avoided. Preferably, the proposed apparatus and method still shall allow a quick and easy encoding and reconstruction of an image of an object of interest.

In a first aspect of the present invention an apparatus for influencing and/or detecting magnetic particles in a field of view, wherein the field of view comprises at least one subfield of interest covering at least a portion of an object of interest, wherein the object of interest contains magnetic particles, and wherein the apparatus has at least two different detection modes, encompassing a high resolution detection mode and a low resolution detection mode, is presented comprising:

selection means comprising a selection field signal generator unit and selection field elements for generating a magnetic selection field having a pattern in space of its magnetic field strength such that a first sub-zone having a low magnetic field strength and a second sub-zone having a higher magnetic field strength are formed in the field of view, wherein in the first sub-zone the magnetization of the magnetic particles is not saturated and wherein in the second sub-zone the magnetization of the magnetic particles is saturated, drive means comprising a drive field signal generator unit and drive field coils for changing the position in space of at least the first sub-zone in the field of view by means of a magnetic drive field so that the magnetization of the magnetic particles contained in said object of interest changes locally, receiving means comprising at least one signal receiving unit and at least one receiving coil for acquiring detection signals, which detection signals depend on the magnetization in at least a portion of the field of view, which magnetization is influenced by the change in the position in space of the at least first sub-zone, a control unit for controlling the signal receiving unit according to the detection mode, wherein in the high resolution detection mode a set of high resolution detection signals is acquired and in the low resolution detection mode a set of low resolution detection signals is acquired, wherein the set of high resolution detection signals depends on the magnetization of at least one subfield of interest and the set of low resolution detection signals depends on the magnetization of at least one adjacent subfield being arranged adjacent to the at least one subfield of interest, and a reconstruction unit for reconstructing a particle distribution quantity characterizing a spatial distribution of the magnetic particles within at least a portion of the object of interest, wherein the particle distribution quantity is reconstructed depending on the set of high resolution detection signals and the set of low resolution detection signals.

In a further aspect of the present invention a method for influencing and/or detecting magnetic particles in a field of view, wherein the field of view comprises at least one subfield of interest covering at least a portion of an object of interest, wherein the object of interest contains magnetic particles, and wherein the magnetic particles can be detected in a high resolution detection mode and in a low resolution detection mode, is presented comprising the steps of:

generating a magnetic selection field having a pattern in space of its magnetic field strength such that a first sub-zone having a low magnetic field strength and a second sub-zone having a higher magnetic field strength are formed in the field of view, wherein in the first sub-zone the magnetization of the magnetic particles is not saturated and wherein in the second sub-zone the magnetization of the magnetic particles is saturated, changing the position in space of at least the first sub-zone in the field of view by means of a magnetic drive field so that the magnetization of the magnetic particles contained in said object of interest changes locally, acquiring detection signals, which detection signals depend on the magnetization in at least a portion of the field of view, which magnetization is influenced by the change in the position in space of the at least first sub-zone, controlling the acquiring of a set of high resolution detection signals in the high resolution detection mode, wherein the set of high resolution detection signals depends on the magnetization of at least one subfield of interest controlling the acquiring of a set of low resolution detection signals in the low resolution detection mode, wherein the set of low resolution detection signals depends on the magnetization of at least one adjacent subfield being arranged adjacent to the at least one subfield of interest, and reconstructing a particle distribution quantity characterizing a spatial distribution of the magnetic particles within at least a portion of the object of interest, wherein the particle distribution quantity is reconstructed depending on the set of high resolution detection signals and the set of low resolution detection signals.

In a still further aspect of the present invention a corresponding computer program is presented comprising program code means for causing a computer to control an apparatus to carry out the steps of said method when said computer program is carried out on the computer.

Preferred embodiments of the invention are defined in the dependent claims. It shall be understood that the claimed method and the claimed computer program have similar and/or identical preferred embodiments as the claimed apparatus and as defined in the dependent claims.

The present invention is based on the idea of acquiring two sets of detection signals. A set of high resolution detection signals depending on the magnetization of at least one subfield of interest and a set of low resolution detection signals depending on the magnetization of at least one adjacent subfield being arranged adjacent to the at least one subfield of interest. Depending on both sets of detection signals a particle distribution quantity characterizing a spatial distribution of the magnetic particles within at least a portion of the object of interest is reconstructed. The particle distribution quantity is finally transmitted to a computer for displaying it on a monitor.

The set of high resolution detection signals characterizes the spectral response of the magnetic nanoparticles arranged in a specific subfield of interest for which a particle distribution quantity and therefore an image shall be reconstructed. Hence, the set of high resolution detection signals contains the proper data needed for reconstructing the particle distribution quantity and thus for reconstructing the image representing the specific subfield of interest. However, as already explained this data is falsified because of contributions in the low frequency components of the high resolution detection signals. Said contributions originate from outside the specific subfield of interest. Therefore, a set of low resolution detection signals is acquired. The set of low resolution detection signals depends on the magnetization of at least one adjacent subfield being adjacent to the specific subfield of interest. Thus, the set of low resolution detection signals contains data that can be used for eliminating the aforementioned falsifications. The set of low resolution detection signals or low resolution data characterizes the spectral response of the magnetic nanoparticles arranged in a number of subfields being adjacent to the specific subfield. Therefore, the low resolution data can be used to correctly assign the detected high resolution detection signals or high resolution data. Thus, falsifications in the high resolution data are eliminated resulting in avoiding artifacts in the image reconstructed for the specific subfield of interest. As the area surrounding the specific subfield of interest is encoded by adjacent subfields, the high resolution detection signals or high resolution data can be correctly assigned. In other words: based on the low resolution detections signals or low resolution data it is possible to identify whether low frequency components contained in the high resolution detection signals or high resolution data originates from the specific subfield of interest or from an adjacent subfield. Hence, low frequency components originating from adjacent subfields and thus artifacts in the image reconstructed for the specific subfield of interest can be eliminated.

As a set of low resolution detection signals or low resolution data is used for eliminating the artifacts in reconstructed images, the additional time needed for determining the data needed for said elimination is not very big. In a low resolution detection mode detection signals can be acquired very quickly. Therefore the proposed apparatus and method still allow a quick and easy encoding and reconstruction of images of an object of interest.

According to a preferred embodiment the drive field signal generator unit is adapted for changing the position in space of the first sub-zone along a defined trajectory, wherein the control unit is adapted for controlling the drive field signal generator unit according to the detection mode, and wherein in the high resolution detection mode the position in space changes along a high resolution trajectory and in the low resolution detection mode the position in space changes along a low resolution trajectory. As already explained, with MPI changes in the magnetization of the nanoparticles needed for reconstructing an image of the examined object are achieved by moving a FFP along a deliberately chosen trajectory. Therefore it is an easy and effective approach to use the trajectories as one, particularly as the main degree of freedom for adjusting or setting the resolution of the MPI apparatus or scanner. Advantageously, besides the drive field signal generator unit also the focus field signal generator unit and/or the selection field signal generator unit are adapted for changing the position in space of the first sub-zone along a defined trajectory.

In a further embodiment of the prior measure, the defined trajectory has the form of a closed Lissajous curve, wherein a first closed Lissajous curve having a first density of trajectory is used as low resolution trajectory and a second Lissajous curve having a second density of trajectory is used as high resolution trajectory, and wherein the first density of trajectory is lower than the second density of trajectory. It turned out that by using closed Lissajous curves simultaneously the best results are obtained with regard to reconstructing the particle distribution quantity and thus an image of the object of interest on the one hand and with regard to setting the resolution of the MPI apparatus or scanner on the other hand. Beyond that, closed Lissajous curves ensure a defined and satisfying covering of a subfield of interest and therefore a reliable acquisition of the detection signals. Further, Lissajous curves can be generated easily. For example in case the drive field coils comprise at least two pairs of drive field coils, the drive field signal generator unit is adapted for controlling a first pair of drive field coils with a first sinusoidal drive field current having a first drive field frequency and a second pair of drive field coils with a second sinusoidal drive field current having a second drive field frequency. For receiving closed Lissajous curves the frequency ratio of the drive field frequencies has to be rational. Advantageously, both drive field frequencies are connected by a frequency ratio $$\frac{N+1}{N}.$$

Thereby, the frequency ratio for the Lissajous curve used in the low resolution detection mode is greater than the frequency ratio for the Lissajous curve used in the high resolution detection mode. The density of trajectory represents the distance existing between the single lines of the trajectory.

Of course, the drive field frequency is not the sole parameter for varying the density of trajectory of closed Lissajous curves and therefore for setting the resolution of the MPI apparatus or scanner. Advantageously, as a further parameter for varying the density of trajectory of closed Lissajous curves a phase position characterizing or influencing the temporal behavior of the sinusoidal drive field current can be used. Thereby, it is conceivable to use the phase position as sole parameter or additional to the drive field frequency for varying the density of trajectory. Particularly, the phase position is used additionally because the density of trajectory can be varied more effective using the drive field frequency than using the phase position. Therefore, in case the phase position is considered as a second parameter, the first pair of drive field coils is controlled with a first sinusoidal drive field current having a first drive field frequency and a first phase position and the second pair of drive field coils is controlled with a second sinusoidal drive field current having a second drive field frequency and a second phase position.

The above explanations concerning varying the density of trajectory of closed Lissajous curves using at least one of the drive field frequency and the phase position refer to 2D-Lissajous curves within a plane. Of course, the above explanations are also applicable to 3D Lissajous curves within a 3D field. In this case the drive field signal generator unit is adapted for controlling a first pair of drive field coils with a first sinusoidal drive field current having a first drive field frequency and a first phase position, a second pair of drive field coils with a second sinusoidal drive field current having a second drive field frequency and a second phase position and a third pair of drive field coils with a third sinusoidal drive field current having a third drive field frequency and a third phase position. With the three drive field frequencies for example the first drive field frequency and the second drive field frequency are connected by a first frequency ratio $$\frac{N}{N-1}$$

and the second drive field frequency and the third drive frequency are connected with a second frequency ratio $$\frac{N+1}{N},$$

wherein N−1 is assigned to the first drive field frequency, N is assigned to the second drive field frequency and N+1 is assigned to the third drive field frequency. Of course for all three sinusoidal drive field currents the individual phase position might be zero.

According to another embodiment, the selection field signal generator unit is adapted for generating a magnetic selection field showing a defined gradient strength, wherein the control unit is adapted for controlling the selection field generator unit according to the detection mode, wherein in the low resolution detection mode a first magnetic selection field showing a first gradient strength is generated and in the high resolution detection mode a second magnetic selection field showing a second gradient strength is generated, and wherein the first gradient strength is smaller than the second gradient strength. With this measure two goals are pursued. Firstly, the resolution of the MPI apparatus or scanner can be influenced, wherein a small gradient strength results in a low resolution and a big gradient strength results in a high resolution. Secondly, the volume of scanning of the MPI scanner can be influenced, wherein a small gradient strength results in an enlarged volume of scanning because of an enlargement of the region the defined trajectory along which the FFP is moved can cover. Thus, choosing a small gradient strength does not only result in a low resolution, but also results in an enlarged volume of scanning. Because of the following reason this combination is advantageous: the set of low resolution detection signals acquired in the low resolution detection mode is used for eliminating artifacts in reconstructed images caused by low frequency contributions originating from outside the specified subfield of interest for which an image shall be reconstructed. It is easily comprehensible that low frequency contributions resulting from the change in magnetization of nanoparticles arranged in the border area of the specific subfield of interest can be acquired much better using an enlarged volume of scanning instead of a normal-sized volume of scanning. With regard to varying or setting the resolution of a MPI apparatus or scanner modifying the trajectory along which the FFP is moved and modifying the gradient strength of the magnetic selection field simultaneously is particularly advantageous.

A further parameter for varying the volume of scanning is the strength and therefore the amplitude of the magnetic drive field, wherein big drive field amplitude results in an enlarged volume of scanning. Advantageously varying the drive field amplitude and varying the gradient strength of the selection field are combined for varying the volume of scanning.

According to a preferred embodiment, the field of view comprises a number of subfields, wherein the drive field signal generator unit is adapted for changing the position in space of the first sub-zone along a defined trajectory having a spatial extent essentially defining the spatial extent of an individual subfield, and wherein the apparatus further comprises focus means comprising a focus field signal generator unit and focus field coils for generating a magnetic focus field for focusing the first sub-zone on an arbitrary subfield contained in the number of subfields. This measure allows the examination of objects and therefore the reconstruction of images for objects that are larger than the volume of scanning specified by the defined trajectory. Thereby, the sequence is as follows: according to the specific subfield of interest for which a set of detection signals shall be acquired a corresponding magnetic focus field is generated focusing the first sub-zone on the specific subfield of interest. Afterwards the first sub-zone or FFP is moved along the defined trajectory within the specific subfield of interest. After the acquisition of the detection signals is completed the magnetic focus field is modified so that the first sub-zone and therefore the defined trajectory is focused on the subfield of interest for which detection signals shall be acquired next. The foregoing explanations are also applicable to adjacent subfields. In case of a subfield of interest, high resolution detection signals are acquired using a high resolution trajectory. In case of an adjacent subfield, low resolution detection signals are acquired using a low resolution trajectory.

In a further embodiment of the prior measure, the control unit is adapted for controlling the focus field signal generator unit for continuously moving the first sub-zone from a first subfield to a second subfield. This measure has the advantage that the magnetic focus field does not show any considerable transient phenomenon while modifying the magnetic focus field for moving the first sub-zone or FFP and therefore the defined trajectory from one subfield to another. Alternatively to this approach a so-called multi-station approach can be used. With a multi-station approach at first a first set of subfields is scanned by continuously moving the first sub-zone from one subfield to another subfield contained in the first set of subfields and then after all subfields contained in the first set of subfields are scanned a second set of subfields is scanned by continuously moving the first sub-zone from one subfield to another subfield contained in the second set of subfields and then after all subfields contained in the second set of subfields are scanned a further set of subfields is scanned and so on. The multi-station approach has the following advantage: as several subfields contained in a set of subfields and therefore being coherent are scanned in sequence for this single set of subfields particle distribution quantities can immediately be reconstructed. Whereas with the first described approach, a greater period of time goes by until the subfields are scanned needed for reconstructing particle distribution quantities for a set of subfields. Of course, moving the first sub-zone continuously must not necessarily result in moving the first sub-zone form one subfield to another. Moving the first sub-zone continuously can be done regardless the subfield structure. For instance, it is conceivable that the first sub-zone is moved continuously for scanning the field of view or a field of interest comprising several subfields of interest line by line, wherein a single line comprises several subfields.

According to another embodiment, the field of view comprises a number of subfields, wherein the set of low resolution detection signals depends on the magnetization of all subfields. This is achieved by controlling the focus field signal generator unit and the drive field signal generator unit so that one single scan is conducted covering the complete field of view and therefore all subfields contained in the field of view. In other words: the total field of view is covered by a fast low resolution scan. The single subfields are encoded using the magnetic drive field for moving the first sub-zone or FFP over the individual subfield region. Advantageously the magnetic drive field has a high drive field frequency and a low drive field amplitude. The repositioning of the subfields is achieved by using the magnetic focus field, wherein the repositioning may be proceeded step-wise or continuously. Advantageously the magnetic focus field has a low focus field frequency and a high focus field amplitude. This measure has the advantage that with one single scan the spatial distribution of the magnetic particles or nanoparticles within each single subfield is recorded. Thus, low resolution data needed for eliminating the above-mentioned falsifications in the high resolution data is available. Hence, any arbitrary subfield can be taken into account as adjacent subfield if necessary. Thereby, it is indifferent whether the concrete subfield that has to be taken into account as adjacent subfield lies inside or outside the field of interest covering the object of interest.

According to another embodiment, the field of view comprises a number of subfields of interest, wherein the set of high resolution detection signals depends on the magnetization of all subfields of interest. This is also achieved by controlling the focus field signal generator unit and the drive field signal generator unit so that one single scan is conducted covering the complete field of interest and therefore all subfields of interest contained in the field of interest. According to the explanations above corresponding to the set of low resolution detection signals, the single subfields of interest are encoded using the magnetic drive field and the repositioning of the subfields of interest is achieved by using the magnetic focus field. This measure has the advantage that with one single scan the spatial distribution of the magnetic nanoparticles within each single subfield of interest is recorded. Thus, high resolution data for every subfield of interest is available.

According to a preferred embodiment, the control unit is adapted for controlling the drive field signal generator unit and the receiving unit for acquiring at first the set of low resolution detection signals and subsequently the set of high resolution detection signals. According to this measure a fast low resolution scan is conducted prior to a high resolution scan. If with regard to the low resolution scan and with regard to the high resolution scan all subfields are considered that are relevant in each case, a fast low-resolution scan of the whole field of view is conducted prior to a high resolution scan of the field of interest. Normally the field of interest is a sub-volume of the field of view. Because of the low resolution scan being conducted in advance information is available that might be of interest with regard to the following high resolution scan. For example, this allows conducting a high resolution scan being adapted to outer circumstances resulting in a better quality of the high resolution detection signals acquired with the high resolution scan or resulting in a saving of time. Advantageously, besides the drive field signal generator unit also the focus field signal generator unit and/or the selection field signal generator unit are controlled by the control unit in an appropriate manner so that at first the set of low resolution detection signals and subsequently the set of high resolution detection signals can be acquired.

According to a preferred embodiment, the field of view comprises a number of subfields, wherein the reconstruction unit comprises a subfield identification unit for identifying at least one subfield of interest and/or for identifying at least one adjacent subfield each comprised in the field of interest. Advantageously, the subfields of interest and/or the adjacent subfields are identified depending on the set of low resolution detection signals acquired with the low resolution scan. It is also conceivable to conduct a particularly adapted survey scan. Compared to the low resolution scan, such a survey scan has a lower resolution and can therefore be conducted in less time. The identification of the subfields is conducted automatically by the subfield identification unit and therefore the MPI apparatus. The subfields are identified depending on object information, more precisely on information about the object of interest. Thereby, in case of the low resolution scan the low resolution detection signals are evaluated. For instance, a subfield is qualified for being a subfield of interest if said subfield is coherent to other subfields showing a comparable low resolution detection signal behavior. Supplementary, further information can be used for identifying the subfields of interest. In case the kind of object to be examined is known per se, predefined information can be considered. For example, such predefined information might represent or characterize the shape of the object to be examined in principle or any other specific property suitable for identifying the object to be examined. Considering predefined information is for example applicable in case a portion of a human body, for example the heart shall be examined.

Advantageously, all subfields of interest and therefore the field of interest are identified. Thus, the field of interest within the field of view is identified for which a high resolution scan shall be conducted allowing a timesaving acquisition of the high resolution detection signals, as the high resolution scan is restricted to the field of interest. Advantageously, subfields being arranged outside the field of interest and covering a further object are identified as adjacent subfields. The further object shall not be coherent with the object of interest or shall represent an object that is in the immediate vicinity of the object of interest but separated form it. Identifying the adjacent subfields helps saving computing power, as for reconstructing the particle distribution quantity adjacent subfields not covering a further object are not taken into account. Identifying the subfields is particularly advantageous in case the low resolution scan is conducted prior to the high resolution scan.

Additionally, depending on the set of low resolution detection signals a particle distribution quantity can be reconstructed. This quantity can be used for displaying the object of interest on a monitor allowing the operator of the MPI apparatus to modify the field of interest identified by the subfield identification unit. The operator can also use the displayed object for positioning purposes, particularly for positioning a patient with regard to the field of view. It is also conceivable to reconstruct a quantity solely representing or characterizing the outline of the object of interest and therefore to solely display this outline instead of displaying the complete object.

In case the reconstruction unit does not comprise a subfield identification unit, it is conceivable to reconstruct a particle distribution quantity depending on the set of low resolution detection signals, wherein this quantity is used for displaying the object of interest or at least the outline of this object on a monitor. In this case, defining the field of interest and positioning the object of interest is done manually by the operator.

The foregoing explanations show, in case no anatomical information from other modalities is available, the set of low resolution detection signals can be used for patient positioning and for defining the region of interest to be scanned with a high resolution scan.

According to a further embodiment, the control unit is adapted for controlling the drive field signal generator unit and the receiving unit for acquiring the set of low resolution detection signals and the set of high resolution detection signals in an interleaved manner. This is a very time-saving approach for acquiring both sets of detection signals. For example, acquiring both sets of detection signals in an interleaved manner can be done as follows: For a first subfield two scans comprising a low resolution scan and a high resolution scan are conducted subsequently. In principle, both scans can be conducted in an arbitrary order, however advantageously the low resolution scan is conducted first followed by the high resolution scan. This order allows for example an adaption of the high resolution scan to outer circumstances. After acquiring the low resolution detection signals and the high resolution detection signals is completed for the first subfield, a low resolution scan and a high resolution scan are conducted for a second subfield, followed by the scans for a third subfield, etc. Advantageously acquiring both sets of detection signals is conducted row by row or column by column, wherein a low resolution scan or high resolution scan is conducted for all subfields of a row or column, followed by a next low resolution or high resolution scan conducted for all subfields of a next row or column. Advantageously, the low resolution scan conducted for a specific subfield does not solely cover the specific subfield but also adjacent subfields being adjacent to the specific subfield. Therefore the low resolution scan also covers an area a surrounding the specific subfield.

According to a further embodiment, the set of high resolution detection signals comprises a number of subsets of high resolution detection signals, each subset being assigned to an individual subfield of interest, wherein the set of low resolution detection signals comprises a number of subsets of low resolution detection signals, each subset being assigned to an individual adjacent subfield, wherein the reconstruction unit is adapted for reconstructing an individual particle distribution quantity for a specific subfield of interest, wherein the individual particle distribution quantity depends on that subset of high resolution detection signals being assigned to the specific subfield of interest and that subsets of low resolution detection signals being assigned to that adjacent subfields being adjacent to the specific subfield of interest. Consequently, the particle distribution quantity is compound of a number of individual particle distribution quantities. This measure ensures an optimal elimination of the falsifications in the reconstructed particle distribution quantity and of the artifacts in the reconstructed image. This is achieved by advantageously considering all adjacent subfields being adjacent to a specific subfield of interest that are qualified for being an origin of low frequency contributions.

According to a further embodiment, the apparatus further comprises a storage unit for storing a first set of system data characterizing the apparatus' low resolution system function and a second set of system data characterizing the apparatus' high resolution system function. Generally, a set of system data is acquired by conducting a calibration measurement timely before the real measurements are conducted for determining a set of detection signals used for reconstructing a particle distribution quantity. With said calibration measurement a so called system function is determined. Said system function establishes the relation between the spatial position of the magnetic particles contained in an object to be examined and the frequency response and therefore the detection signals acquired with the receiving means. The system function describes inherently the properties of the MPI scanner, in particular fields generated by the unloaded coils, and the properties of the contrast agent used. A calibration measurement has to be done once for a setup of coils and a contrast agent. As already mentioned, the MPI apparatus or scanner has a high resolution detection mode and a low resolution detection mode. In both detection modes different trajectories are used for acquiring the detection signals. Therefore two different sets of system data has to be determined. With a first calibration measurement using a low resolution trajectory a first set of system data and with a second calibration measurement using a high resolution trajectory a second set of system data is determined. Alternatively, instead of conducting a calibration measurement for determining the set of system data, these data can also be calculated using for example a model based approach. Calculating the set of system data is less time-consuming than measuring the set of system data by conducting a calibration measurement. Particularly for the first set of system data characterizing the apparatus' low resolution system function calculating the set of system data is a possibility.

As already explained, the object to be examined using a MPI system must contain magnetic particles. If the object is an animal or a patient, said magnetic particles get into the object or body by administering a contrast agent containing such magnetic particles. Hence a distribution of magnetic particles within a body can also be considered as a distribution of the contrast agent.

In the explanations above and below the terms "sub-volume" and "subfield" are used synonymously. The same applies to other combined terms containing the terms "volume" and "field", for example "field of interest" and "volume of interest". This shall not necessarily imply that the term "field" only stands for a three-dimensional object. The term "field" shall cover two-dimensional objects, too.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Before the details of the present invention shall be explained, basics of magnetic particle imaging shall be explained in detail with reference to FIGS. 1 to 4. In particular, two embodiments of an MPI scanner for medical diagnostics will be described. An informal description of the data acquisition is also given. The similarities and differences between the two embodiments will be pointed out.

Figure 1:
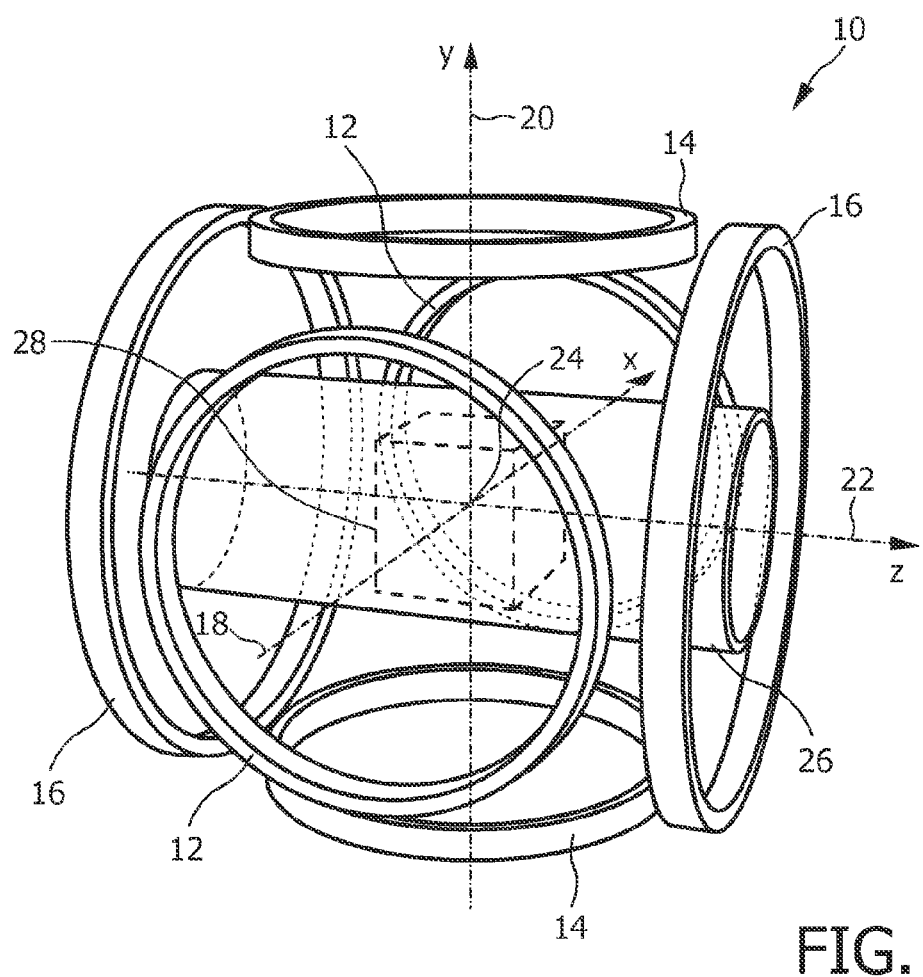
FIG. 1 shows a first embodiment of an MPI apparatus.

The first embodiment 10 of an MPI scanner shown in FIG. 1 has three prominent pairs 12, 14, 16 of coaxial parallel circular coils, each pair being arranged as illustrated in FIG. 1. These coil pairs 12, 14, 16 serve to generate the selection field as well as the drive and focus fields. The axes 18, 20, 22 of the three coil pairs 12, 14, 16 are mutually orthogonal and meet in a single point, designated the isocenter 24 of the MPI scanner 10. In addition, these axes 18, 20, 22 serve as the axes of a 3D Cartesian x-y-z coordinate system attached to the isocenter 24. The vertical axis 20 is nominated the y-axis, so that the x and z-axes are horizontal. The coil pairs 12, 14, 16 are also named after their axes. For example, the y-coil pair 14 is formed by the coils at the top and the bottom of the scanner. Moreover, the coil with the positive (negative) y-coordinate is called the $y^+$-coil ($y^-$-coil), and similarly for the remaining coils.

The scanner 10 can be set to direct a predetermined, time dependent electric current through each of these coils 12, 14, 16, and in either direction. If the current flows clockwise around a coil when seen along this coil's axis, it will be taken as positive, otherwise as negative. To generate the static selection field, a constant positive current $I^S$ is made to flow through the $z^+$-coil, and the current $-I^S$ is made to flow through the $z^-$-coil. The z-coil pair 16 then acts as an anti-parallel circular coil pair.

Figure 2:
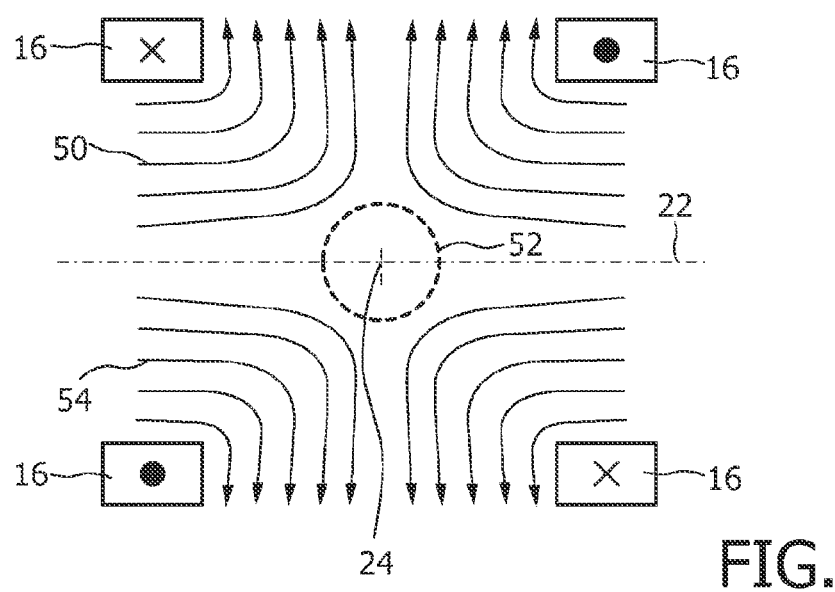
FIG. 2 shows an example of the selection field pattern produced by an apparatus as shown in FIG. 1.

The magnetic selection field which is generally a gradient magnetic field is represented in FIG. 2 by the field lines 50. It has a substantially constant gradient in the direction of the (e.g. horizontal) z-axis 22 of the z-coil pair 16 generating the selection field and reaches the value zero in the isocenter 24 on this axis 22. Starting from this field-free point (not individually shown in FIG. 2), the field strength of the magnetic selection field characterized by the field lines 50 increases in all three spatial directions as the distance increases from the field-free point. In a first sub-zone or region 52 which is denoted by a dashed line around the isocenter 24 the field strength is so small that the magnetization of particles present in that first sub-zone 52 is not saturated, whereas the magnetization of particles present in a second sub-zone 54 (outside the region 52) is in a state of saturation. The first sub-zone 52 of the scanner's field of view 28 is preferably a spatially coherent area. The same applies to the field-free point contained in the first sub-zone 52. The first sub-zone 52 may also be a punctiform area, a line or a flat area. In the second sub-zone 54 (i.e. in the residual part of the scanner's field of view 28 outside of the first sub-zone 52) the magnetic field strength of the selection field is sufficiently strong to keep the magnetic particles in a state of saturation.

By changing the position of the two sub-zones 52, 54 within the field of view 28 the (overall) magnetization in the field of view 28 changes. By measuring the magnetization in the field of view 28 or physical parameters influenced by the magnetization, information about the spatial distribution of the magnetic particles in the field of view 28 can be obtained. In order to change the relative spatial position of the two sub-zones 52, 54 in the field of view 28, further magnetic fields, i.e. the magnetic drive field, and, if applicable, the magnetic focus field, are superimposed to the selection field characterized by the field lines 50 in the field of view 28 or at least in a part of the field of view 28.

To generate the drive field, a time dependent current $I^D_1$ is made to flow through both x-coils 12, a time dependent current $I^D_2$ through both y-coils 14, and a time dependent current $I^D_3$ through both z-coils 16. Thus, each of the three coil pairs acts as a parallel circular coil pair. Similarly, to generate the focus field, a time dependent current $I^F_1$ is made to flow through both x-coils 12, a current $I^F_2$ through both y-coils 14, and a current $I^F_3$ through both z-coils 16.

It should be noted that the z-coil pair 16 is special: It generates not only its share of the drive and focus fields, but also the selection field. The current flowing through the $z^\pm$-coil is $I^D_3+I^F_3+I^S$. The current flowing through the remaining two coil pairs 12, 14 is $I^D_k+I^F_k$, k=1, 2. Because of their geometry and symmetry, the three coil pairs 12, 14, 16 are well decoupled. This is wanted.

Being generated by an anti-parallel circular coil pair, the selection field is rotationally symmetric about the z-axis, and its z-component is nearly linear in z and independent of x and y in a sizeable volume around the isocenter 24. In particular, the selection field has a single field free point (FFP) at the isocenter. In contrast, the contributions to the drive and focus fields, which are generated by parallel circular coil pairs, are spatially nearly homogeneous in a sizeable volume around the isocenter 24 and parallel to the axis of the respective coil pair. The drive and focus fields jointly generated by all three parallel circular coil pairs are spatially nearly homogeneous and can be given any direction and strength, up to some maximum strength. The drive and focus fields are also time dependent. The difference between the focus field and the drive field is that the focus field varies slowly in time and has a large amplitude while the drive field varies rapidly and has a small amplitude. There are physical and biomedical reasons to treat these fields differently. A rapidly varying field with a large amplitude would be difficult to generate and hazardous to the patient.

The MPI scanner 10 has at least one further pair, preferably three further pairs, of parallel circular coils, again oriented along the x-, y-, and z-axes. These coil pairs, which are not shown in FIG. 1, serve as receive coils. As with the coil pairs 12, 14, 16 for the drive and focus fields, the magnetic field generated by a constant current flowing through one of these receive coil pairs is spatially nearly homogeneous within the field of view and parallel to the axis of the respective coil pair.

The receive coils are supposed to be well decoupled. The time dependent voltage induced in a receive coil is amplified and sampled by a receiver attached to this coil. More precisely, to cope with the enormous dynamic range of this signal, the receiver samples the difference between the received signal and a reference signal. The transfer function of the receiver is non-zero from DC up to the point where the expected signal level drops below the noise level.

The MPI scanner 10 shown in FIG. 1 has a cylindrical bore 26 along the z-axis 22, i.e. along the axis of the selection field. All coils are placed outside this bore 26. For the data acquisition, the patient (or object) to be imaged (or treated) is placed in the bore 26 such that the patient's volume of interest—that volume of the patient (or object) that shall be imaged (or treated)—is enclosed by the scanner's field of view 28—that volume of the scanner whose contents the scanner can image. The patient (or object) is, for instance, placed on a patient table. The field of view 28 is a geometrically simple, isocentric volume in the interior of the bore 26, such as a cube, a ball, or a cylinder. A cubical field of view 28 is illustrated in FIG. 1.

The size of the first sub-zone 52 is dependent on the one hand on the strength of the gradient of the magnetic selection field and on the other hand on the field strength of the magnetic field required for saturation. For a sufficient saturation of the magnetic particles at a magnetic field strength of 80 A/m and a gradient (in a given space direction) of the field strength of the magnetic selection field amounting to $50 \times 10^3$ A/m$^2$, the first sub-zone 52 in which the magnetization of the particles is not saturated has dimensions of about 1 mm (in the given space direction).

The patient's volume of interest is supposed to contain magnetic nanoparticles. Especially prior to a therapeutic and/or diagnostic treatment of, for example, a tumor, the magnetic particles are positioned in the volume of interest, e.g. by means of a liquid comprising the magnetic particles which is injected into the body of the patient (object) or otherwise administered, e.g. orally, to the patient. The liquid comprising the magnetic particles is called contrast agent.

An embodiment of magnetic particles comprises, for example, a spherical substrate, for example, of glass which is provided with a soft-magnetic layer which has a thickness of, for example, 5 nm and consists, for example, of an iron-nickel alloy (for example, Permalloy). This layer may be covered, for example, by means of a coating layer which protects the particle against chemically and/or physically aggressive environments, e.g. acids. The magnetic field strength of the magnetic selection field 50 required for the saturation of the magnetization of such particles is dependent on various parameters, e.g. the diameter of the particles, the used magnetic material for the magnetic layer and other parameters.

In the case of e.g. a diameter of 10 μm, a magnetic field of approximately 800 A/m (corresponding approximately to a flux density of 1 mT) is then required, whereas in the case of a diameter of 100 μm a magnetic field of 80 A/m suffices. Even smaller values are obtained when a coating of a material having a lower saturation magnetization is chosen or when the thickness of the layer is reduced. Magnetic particles that can generally be used are available on the market under the trade name Resovist.

For further details of the generally usable magnetic particles and particle compositions, the corresponding parts of EP 1304542, WO 2004/091386, WO 2004/091390, WO 2004/091394, WO 2004/091395, WO 2004/091396, WO 2004/091397, WO 2004/091398, WO 2004/091408 are herewith referred to, which are herein incorporated by reference. In these documents more details of the MPI method in general can be found as well.

The data acquisition starts at time $t_s$ and ends at time $t_e$. During the data acquisition, the x-, y-, and z-coil pairs 12, 14, 16 generate a position- and time dependent magnetic field, the applied field. This is achieved by directing suitable currents through the coils. In effect, the drive and focus fields push the selection field around such that the FFP moves along a pre-selected FFP trajectory that traces out the volume of scanning—a superset of the field of view. The applied field orientates the magnetic nanoparticles in the patient. As the applied field changes, the resulting magnetization changes too, though it responds nonlinearly to the applied field. The sum of the changing applied field and the changing magnetization induces a time dependent voltage $V_k$ across the terminals of receive coil pair along the $x_k$-axis. The associated receiver converts this voltage to a signal $S_k(t)$, which it samples and outputs.

It is advantageous to receive or to detect signals from the magnetic particles located in the first sub-zone 52 in another frequency band (shifted to higher frequencies) than the frequency band of the magnetic drive field variations. This is possible because frequency components of higher harmonics of the magnetic drive field frequency occur due to a change in magnetization of the magnetic particles in the scanner's field of view 28 as a result of the non-linearity of the magnetization characteristics.

Figure 3:
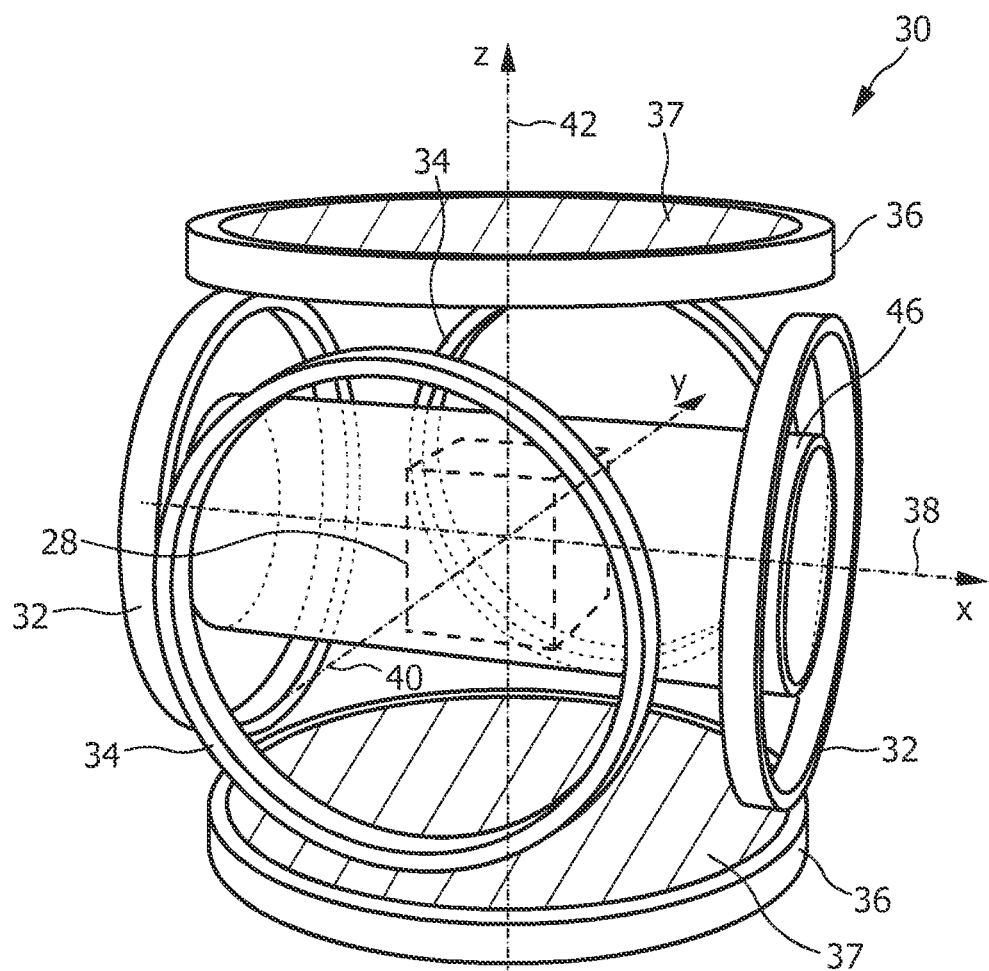
FIG. 3 shows a second embodiment of an MPI apparatus.

FIG. 3 shows a second embodiment of a MP scanner 30. Like the first embodiment shown in FIG. 1, the second embodiment of the MPI scanner 30 has three circular and mutually orthogonal coil pairs 32, 34, 36, but these coil pairs 32, 34, 36 generate the selection field and the focus field only. The z-coils 36, which again generate the selection field, are filled with ferromagnetic material 37. The z-axis 42 of this embodiment 30 is oriented vertically, while the x- and y-axes 38, 40 are oriented horizontally. The bore 46 of the scanner is parallel to the x-axis 38 and, thus, perpendicular to the axis 42 of the selection field. The bore 46 contains a field of view 28. The drive field is generated by a solenoid (not shown) along the x-axis 38 and by pairs of saddle coils (not shown) along the two remaining axes 40, 42. These coils are wound around a tube which forms the bore. The drive field coils also serve as receive coils. The signals picked up by the receive coils are sent through a high-pass filter that suppresses the contribution caused by the applied field.

To give a few typical parameters of such an embodiment: The z-gradient of the selection field, G, has a strength of $G/\mu_0 = 2.5$ T/m, where $\mu_0$ is the vacuum permeability.

The selection field generated does either not vary at all over the time or the variation is comparably slow, preferably between approximately 1 Hz and approximately 100 Hz. The temporal frequency spectrum of the drive field is concentrated in a narrow band around 25 kHz (up to approximately 100 kHz). The useful frequency spectrum of the received signals lies between 50 kHz and 1 MHz (eventually up to approximately 10 MHz). The bore has a diameter of 120 mm. The biggest cube that fits into the bore 46 has an edge length of 120 mm/$\sqrt{2} \approx 84$ mm.

As shown in the above embodiments the various magnetic fields can be generated by coils of the same coil pairs and by providing these coils with appropriately generated currents. However, and especially for the purpose of a signal interpretation with a higher signal to noise ratio, it may be advantageous when the temporally constant (or quasi constant) selection field and the temporally variable drive field and focus field are generated by separate coil pairs. Generally, coil pairs of the Helmholtz type can be used for these coils, which are generally known, e.g. from the field of magnetic resonance apparatus with open magnets (open MRI) in which a radio frequency (RF) coil pair is situated above and below the region of interest, said RF coil pair being capable of generating a temporally variable magnetic field. Therefore, the construction of such coils need not be further elaborated herein.

In an alternative embodiment for the generation of the selection field, permanent magnets (not shown) can be used. In the space between two poles of such (opposing) permanent magnets (not shown) there is formed a magnetic field which is similar to that shown in FIG. 2, that is, when the opposing poles have the same polarity. In another alternative embodiment, the selection field can be generated by a mixture of at least one permanent magnet and at least one coil.

Figure 4:
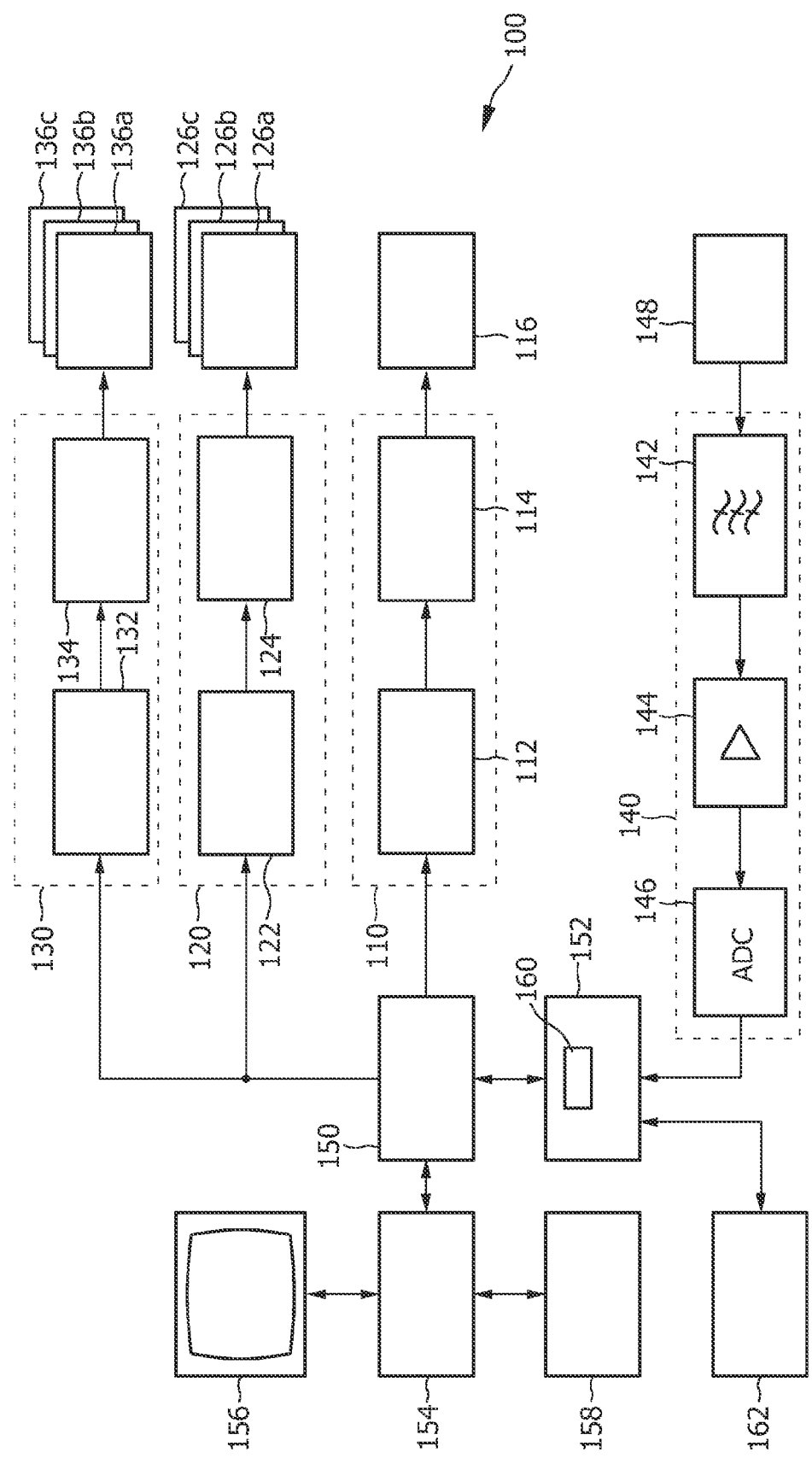
FIG. 4 shows a block diagram of an MPI apparatus according to the present invention.

FIG. 4 shows a general block diagram of an MPI apparatus 100 according to the present invention. The apparatus 100 allows influencing and/or detecting of magnetic particles in a field of view 28. Said magnetic particles are contained in an object, wherein the object might be a human or animal body. The general principles of magnetic particle imaging and of magnetic resonance imaging explained above are valid and applicable to this embodiment as well, unless otherwise specified.

The apparatus 100 has at least two different detection modes for detecting the magnetic particles, encompassing a high resolution detection mode and a low resolution detection mode. With regard to the invention, a control unit 150 selects the appropriate detection mode and generates corresponding control signals. Nevertheless, the possibility shall exist for an operator of the apparatus 100 to select a detection mode according to his demand, for example by using a input unit 158. But as this is not the basic point of the invention this issue will not be further discussed.

The embodiment of the apparatus 100 shown in FIG. 4 comprises a set of various coils for generating the desired magnetic fields. First, the coils and their functions in a MPI mode shall be explained.

For generating the magnetic (gradient) selection field explained above, selection means are provided comprising a set of selection field (SF) coils 116, preferably comprising at least one pair of coil elements. The selection means further comprises a selection field signal generator unit 110. Preferably, a separate generator subunit is provided for each coil element (or each pair of coil elements) of the set 116 of selection field coils. Said selection field signal generator unit 110 comprises a controllable selection field current source 112 (generally including an amplifier) and a filter unit 114 which provide the respective section field coil element with the selection field current to individually set the gradient strength of the selection field in the desired direction. Preferably, a DC current is provided. If the selection field coil elements are arranged as opposed coils, e.g. on opposite sides of the field of view, the selection field currents of opposed coils are preferably oppositely oriented. With said selection means a magnetic selection field having a pattern in space of its magnetic field strength such that a first sub-zone 52 having a low magnetic field strength and a second sub-zone 54 having a higher magnetic field strength are formed in a field of view 28, as it is shown in FIG. 2.

The selection field signal generator unit 110 is controlled by the control unit 150, which preferably controls the selection field current generation 110 such that the sum of the field strength and the sum of the gradient strength of all spatial fractions of the selection field is maintained at a predefined level. In doing so, the control unit 150 controls the selection field generator unit 110 according to the detection mode, wherein in the low resolution detection mode a first magnetic selection field showing a first gradient strength and in the high resolution detection mode a second magnetic selection field showing a second gradient strength is generated. The first gradient strength is smaller than the second gradient strength. Thereby, two effects are used. A small gradient strength of the magnetic selection field results in a low resolution and in an enlarged volume of scanning Primarily, the selection field current source 112 contained in the selection field signal generator unit 110 is controlled by the control unit 150.

For generation of a magnetic focus field the apparatus 100 further comprises focus means comprising a set of focus field (FF) coils, preferably comprising three pairs 126*a*, 126*b*, 126*c* of oppositely arranged focus field coil elements. Said magnetic focus field is generally used for changing the position in space of the region of action. In other words: the focus means allow focusing the first sub-zone 52 on an arbitrary subfield contained in the field of view 28. Thus, although the defined trajectory only has a limited spatial extent that essentially defines the spatial extent of an individual subfield, it is possible to examine objects and therefore to reconstruct images for objects that are larger than the volume of scanning specified by the defined trajectory.

The focus field coils are controlled by a focus field signal generator unit 120, preferably comprising a separate focus field signal generation subunit for each coil element (or at least each pair of coil elements) of said set of focus field coils. Said focus field signal generator unit 120 comprises a focus field current source 122 (preferably comprising a current amplifier) and a filter unit 124 for providing a focus field current to the respective coil of said subset of coils 126*a*, 126*b*, 126*c* which shall be used for generating the magnetic focus field. The focus field current unit 120 is also controlled by the control unit 150. Primarily, the focus field current source 122 contained in the focus field signal generator unit 120 is controlled by the control unit 150. It is thinkable that the control unit 150 is adapted for controlling the focus field signal generator unit 120 for continuously moving the first sub-zone 52 from a first subfield to a second subfield contained in the field of view 28. Otherwise, the first sub-zone is moved in a multi-station approach.

For generation of the magnetic drive field the apparatus 100 further comprises drive means comprising a subset of drive field (DF) coils, preferably comprising three pairs 136*a*, 136*b*, 136*c* of oppositely arranged drive field coil elements. The drive field coils are controlled by a drive field signal generator unit 130, preferably comprising a separate drive field signal generation subunit for each coil element (or at least each pair of coil elements) of said set of drive field coils. Said drive field signal generator unit 130 comprises a drive field current source 132 (preferably including a current amplifier) and a filter unit 134 for providing a drive field current to the respective drive field coil. The drive field current source 132 is adapted for generating an AC current and is also controlled by the control unit 150. With said drive means the position in space of the two sub-zones 52, 54 in the field of view 28 can be changed by means of a magnetic drive field so that the magnetization of the magnetic particles contained in said object changes locally. Primarily, the drive field current source 132 contained in the drive field signal generator unit 130 is controlled by the control unit 150.

The drive field signal generator unit 130 is adapted for changing the position in space of the first sub-zone 52 along a defined trajectory. In doing so, the control unit 150 is adapted for controlling the drive field signal generator unit 130 according to the detection mode, wherein in the high resolution detection mode the position in space changes along a high resolution trajectory and in the low resolution detection mode the position in space changes along a low resolution trajectory. The defined trajectory has the form of a closed Lissajous curve, wherein a first closed Lissajous curve having a first density of trajectory is used as low resolution trajectory and a second Lissajous curve having a second density of trajectory is used as high resolution trajectory. The first density of trajectory is lower than the second density of trajectory.

For moving the FFP along a defined trajectory or for changing the position in space of the first sub-zone 52 along a defined trajectory a sequence of varying currents has to flow in the drive field coils 136*a*, 136*b*, 136*c*. In case of a 2D Lissajous curve two of the drive field coils 136*a*, 136*b*, 136*c* are controlled with sinusoidal drive field currents. The 2D Lissajous curve is generated by superposition of two orthogonal harmonic drive fields. For instance a first drive field coil generating a magnetic drive field in direction of the x-axis and a second drive field coil generating a magnetic drive field in direction of the y-axis are controlled. The first drive field coil is controlled with a first drive field current having the form $I_x = \hat{I}_x \sin(\omega_x t)$, wherein $\hat{I}_x$ is a first drive field amplitude and $\omega_x$ is a first drive field frequency. The second drive field coil is controlled with a second drive field current having the form $I_y = \hat{I}_y \sin(\omega_y t)$, wherein $\hat{I}_y$ is a second drive field amplitude and $\omega_y$ is a second drive field frequency. For receiving closed Lissajous curves the frequency ratio of both drive field frequencies has to be rational. Advantageously, both drive field frequencies fulfill the frequency ratio condition $$\frac{\omega_x}{\omega_y} = \frac{N+1}{N}.$$

The closed 2D Lissajous curve lies within the x-y-plane. Of course appropriate closed 2D Lissajous curves in any other plane may be generated by appropriate currents flowing through the corresponding drive field coils. Advantageously the 2D Lissajous figure existing in the x-y-plane is moved in z-direction by creating an appropriate magnetic focus field, resulting in a 3D trajectory.

The frequency ratio for the closed Lissajous curve used in the low resolution detection mode is greater than the frequency ratio for the closed Lissajous curve used in the high resolution detection mode. For example the following frequency ratios are chosen:

$$\frac{\omega_x}{\omega_y} = \frac{11}{10}$$

for the Lissajous curve used in the low resolution detection mode and $$\frac{\omega_x}{\omega_y} = \frac{51}{50}$$

for the Lissajous curve used in the high resolution detection mode. Of course any other favorable frequency ratios can be chosen.

For signal detection the apparatus 100 further comprises receiving means comprising a receiving coil 148 and a signal receiving unit 140, which receives signals detected by said receiving coil 148. Said signal receiving unit 140 comprises a filter unit 142 for filtering the received detection signals. The aim of this filtering is to separate measured values, which are caused by the magnetization in the examination area which is influenced by the change in position of the two part-regions 52, 54, from other, interfering signals. To this end, the filter unit 142 may be designed for example such that signals which have temporal frequencies that are smaller than the temporal frequencies with which the receiving coil 148 is operated, or smaller than twice these temporal frequencies, do not pass the filter unit 142. The signals are then transmitted via an amplifier unit 144 to an analog/digital converter 146 (ADC). The digitalized signals produced by the analog/digital converter 146 are fed to a reconstruction unit 152 (also called image processing unit). Thus, with the receiving means detection signals are acquired. Said detection signals depend on the magnetization in the field of view 28, which magnetization is influenced by the change in the position in space of the first and second sub-zone 52, 54. Said detection signals are forwarded in a digitized form to the reconstruction unit 152.

The reconstruction unit 152 reconstructs the spatial distribution of the magnetic particles from the detection signals received from the signal receiving unit 140 and from the respective position which the first part-region 52 takes up in the examination area at that time at which the detection signal to be processed was acquired with the receiving means. The reconstruction unit 152 obtains the position from the control unit 150. The reconstructed spatial distribution of the magnetic particles is finally transmitted via the control unit 150 to a computer 154, which displays it on a monitor 156. Thus, an image can be displayed showing the distribution of magnetic particles in the field of view of the examination area. Thus, with the reconstruction unit 152 a particle distribution quantity characterizing the spatial distribution of the magnetic particles within at least a portion of the object to be examined is determined depending on the detection signals. The particle distribution quantity is forwarded to the computer 154 via the control unit 150.

Further, an input unit 158 is provided, for example a keyboard. A user is therefore able to set the desired direction of the highest resolution and in turn receives the respective image of the region of action on the monitor 156. If the critical direction, in which the highest resolution is needed, deviates from the direction set first by the user, the user can still vary the direction manually in order to produce a further image with an improved imaging resolution. This resolution improvement process can also be operated automatically by the control unit 150 and the computer 154. The control unit 150 in this embodiment sets the gradient field in a first direction which is automatically estimated or set as start value by the user. The direction of the gradient field is then varied stepwise until the resolution of the thereby received images, which are compared by the computer 154, is maximal, respectively not improved anymore. The most critical direction can therefore be found respectively adapted automatically in order to receive the highest possible resolution.

The apparatus 100 further comprises a storage unit 162 for storing a first set of system data characterizing the apparatus' low resolution system function and a second set of system data characterizing the apparatus' high resolution system function. Two sets of system data have to be stored because of the two different detection modes in which the MPI apparatus 100 can be operated. Each of both sets of system data is acquired by conducting a calibration measurement timely before the real measurements are conducted for acquiring the detection signals for reconstructing the particle distribution quantity. The reconstruction unit 152 contains a subfield identification unit 160 for identifying the subfields of interest and/or the adjacent subfields within the field of view 28. So it is possible to define the field of interest within the field of view 28 for which a high resolution scan shall be conducted.

According to the invention the control unit 150 is adapted for controlling the signal receiving unit 140 according to the detection mode. In the high resolution detection mode a set of high resolution detection signals is acquired, wherein the set of high resolution detection signals depends on the magnetization of at least one subfield of interest, In the low resolution detection mode a set of low resolution detection signals is acquired, wherein the set of low resolution detection signals depends on the magnetization of at least one adjacent subfield being arranged adjacent to the at least one subfield of interest. Controlling the receiving unit 140 means for example adjusting the frequency characteristic of the filter unit 142 and/or adjusting the amplification characteristic of the amplifier unit 144 and/or adjusting the sampling characteristic of the analog/digital converter 146 to the detection mode. With the reconstruction unit 152 a particle distribution quantity characterizing a spatial distribution of the magnetic particles within at least a portion of the object of interest is reconstructed, wherein the particle distribution quantity is reconstructed depending on the set of high resolution detection signals and the set of low resolution detection signals.

Besides the receiving unit 140 also the drive field signal generator unit 130 and the selection field generator unit 110 are controlled by the control unit 150 according to the detection mode.

On the computer 154 a computer program is carried out, wherein said computer program comprises program code means for causing the computer 154 to control the apparatus 100 to carry out the steps of a method according to the invention.

Figure 5:
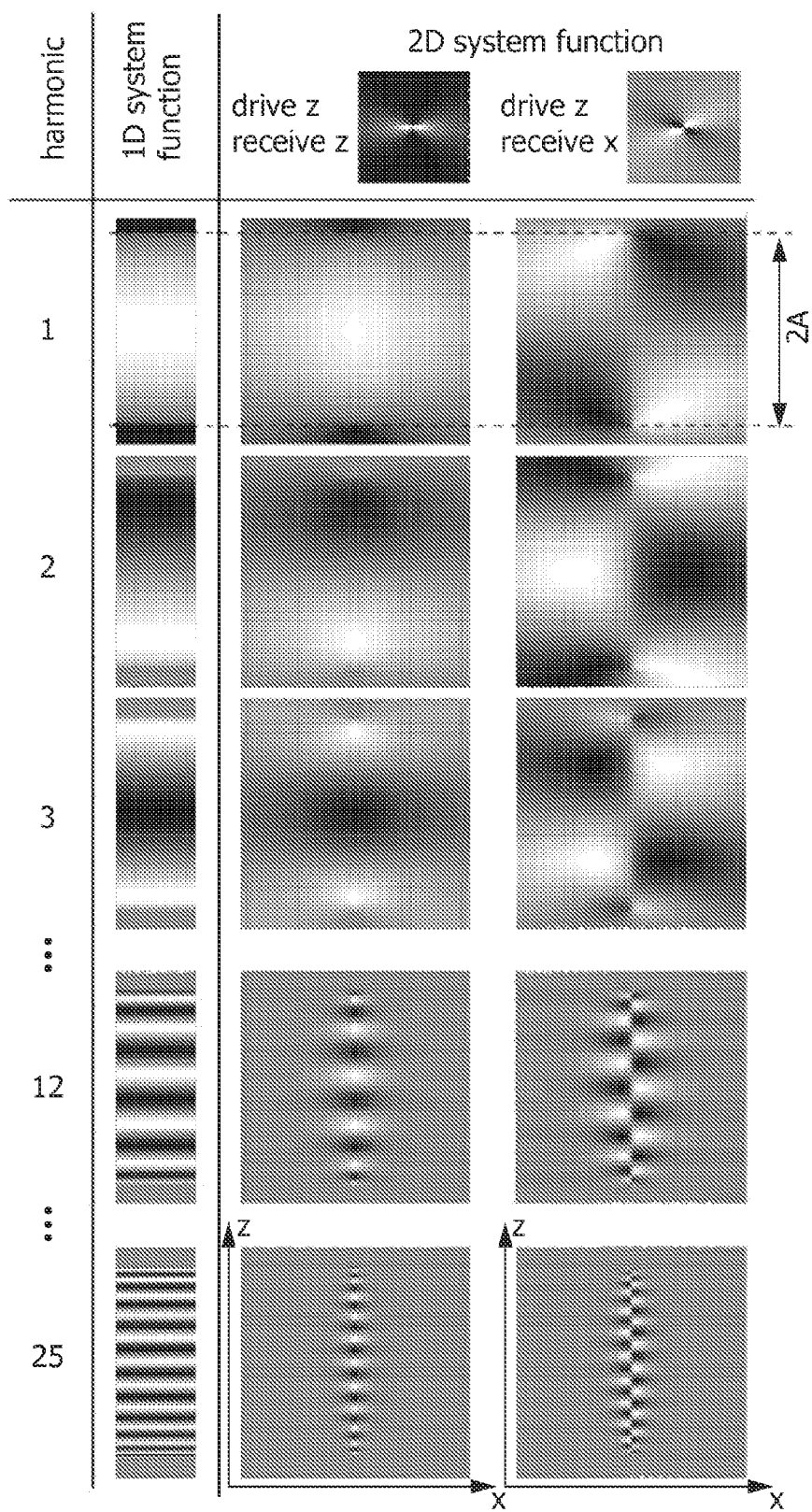
FIG. 5 shows diagrams illustrating the ideal system function response at different harmonics to a 1D FFP motion along the center line in z direction, FIG. 6 schematically shows a plane contained in a field of view.

FIG. 5 shows the spatial extension of the system function response to a vertical line trajectory of the FFP or the first sub-zone 52 orientated in the z-direction. Concretely, central 1D and 2D slices extracted from selected harmonics are shown. The system function establishes the relation between the spatial position of the magnetic particles contained in an object to be examined and the frequency response and therefore the detection signals acquired with the receiving means. As can be seen, the system function response is not completely localized. At low frequencies, especially harmonics 1 to 3, the response and therefore the sensitive region is extended quite laterally, whereas at higher frequencies, especially harmonics 12 and 25, the response and therefore the sensitive region is located close to the line of the FFP motion. The delocalization of the low frequency components is the reason why signals from outside a specific subfield for which high resolution detection signals are acquired signals are picked up. If the area surrounding the specific subfield is not encoded by other subfields, the signals picked up cannot be correctly assigned. The falsification in the set of high resolution detection signals caused by the signals picked up results in severe artifacts in the reconstructed image.

Figure 6:
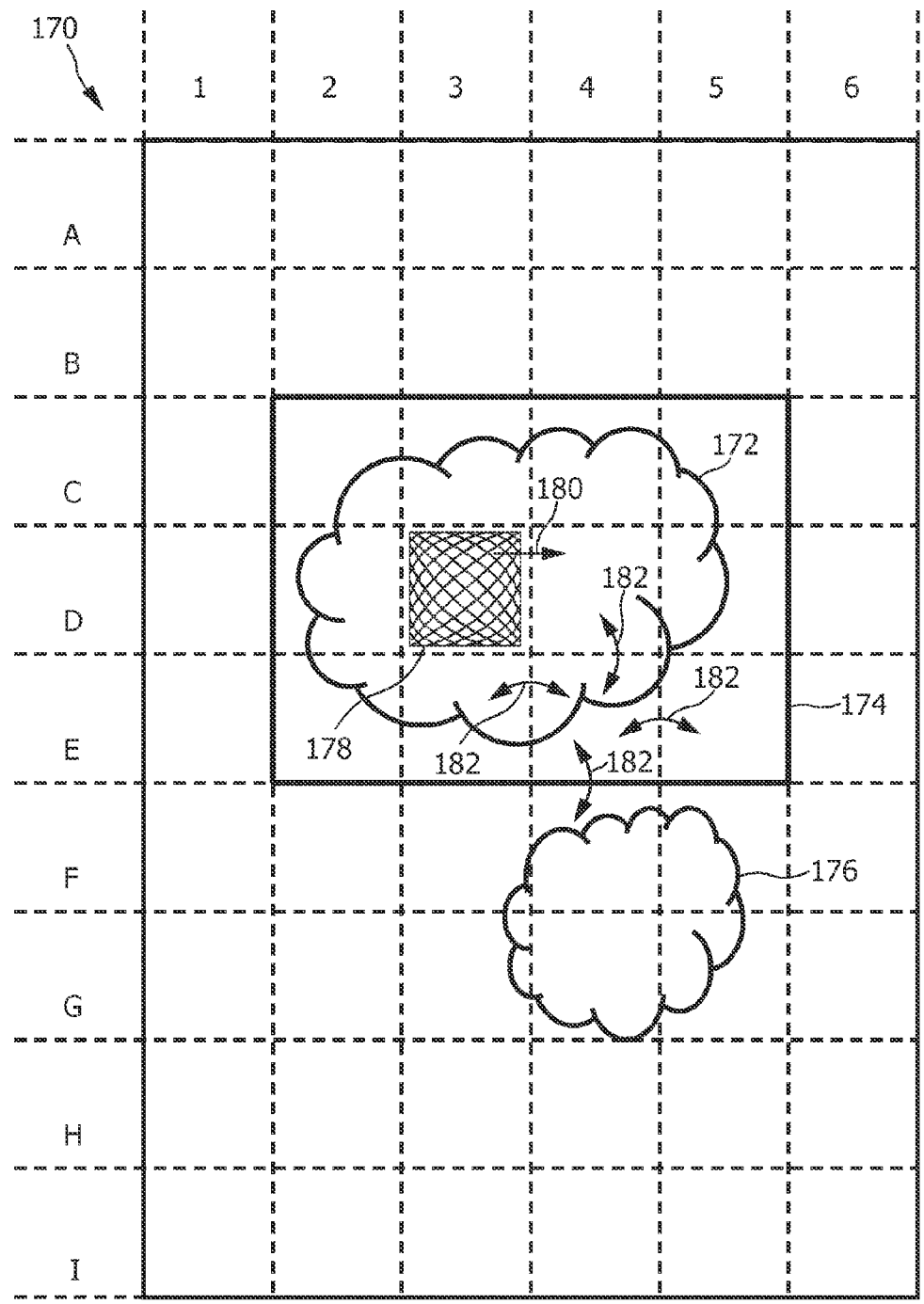

FIG. 6 schematically shows a 2D field of view 170, wherein the 2D field of view 170 represents a plane contained in the field of view 28. The 2D field of view 170 consists of a number of subfields being arranged in rows and columns. For the sake of clarity the rows are labeled with letters A to I and the columns are labeled with numbers 1 to 6. Therefore, each single subfield can be identified with a tuple existing of a letter and a number starting with "A1" and ending at "I6".

The 2D field of view 170 covers an object of interest 172 being the object to be examined with the apparatus 100. Those subfields of the 2D field of view 170 that cover at least a portion of the object of interest 172 are referred to as subfields of interest. The subfields of interest form a field of interest 174. In the present example, the subfields of interest are the subfields C2, C3, C4, C5, D2, D3, D4, D5, E2, E3, E4 and E5. With the apparatus 100 a set of high resolution detection signals is acquired depending on the magnetization of said subfields of interest.

Besides the object of interest 172, the 2D field of view 170 also covers a further object 176. For the further object 176 a set of high resolution detection signals shall not be acquired.

The set of high resolution detection signals corresponding to the object of interest 172 is acquired by conducting a high resolution scan for the field of interest 174. According to the specific subfield of interest for which a subset of high resolution detection signals shall be acquired first a corresponding magnetic focus field is generated focusing the first sub-zone 52 on the specific subfield of interest, in the present example subfield D3. Afterwards the first sub-zone 52 or FFP is moved along a defined trajectory 178 within the specific subfield of interest D3. After acquisition of the subset of high resolution detection signals for the specific subfield D3 is completed the magnetic focus field is modified so that the first sub-zone 52 is focused on that subfield of interest for which a subset of high resolution detection signals shall be acquired next, in the present case subfield D4. Modification of the focus field and therefore moving the first sub-zone 52 from subfield D3 to subfield D4 is indicated by an arrow 180. The steps of modifying the focus field and of moving the first sub-zone 52 or FFP along a defined trajectory are alternately repeated until for all subfields of interest the respective subset of high resolution detection signals is acquired.

Trajectory 178 shown in FIG. 6 is only exemplary. The course of trajectory 178 shall not have any restricting impact, for example on the frequency ratio of the drive field currents flowing through the drive field coils 136a, 136b, 136c for generating closed Lissajous curves.

The set of high resolution detection signals acquired for the field of interest 174 contains the proper data needed for reconstructing the particle distribution quantity and thus for reconstructing the image representing the object of interest 172. However, this data is falsified because of contributions in the low frequency components of the high resolution detection signals. Said contributions originate from outside the specific subfield of interest, namely from adjacent subfields being adjacent to the specific subfield. Thereby, not only adjacent subfields being arranged outside the field of interest 174 come into question, but also adjacent subfields being arranged inside the field of interest 174. For example, for the specific subfield of interest E4 the subfields D3, D4, D5, E3, E5, F3, F4 and F5 are adjacent subfields with regard to said contributions in the low frequency components. Thus, for the specific subfield of interest E4 there exist eight adjacent subfields, namely four orthogonal adjacent subfields D4, E3, E5 and F4 and four diagonal adjacent subfields D3, D5, F3 and F5. In case the specific subfield is located on the edge of the 2D field of view 170 or in a corner of the 2D field of view 170 the number of adjacent subfields is less. With regard to a two-dimensional field of view an orthogonal adjacent subfield has an edge in common with the specific subfield of interest, whereas a diagonal adjacent subfield solely has a corner in common with the specific subfield of interest. The subfields being adjacent to the specific subfield E4 are indicated with arrows 182, whereas for the sake of clarity solely the adjacent orthogonal subfields are marked. This shall not have any restricting impact.

The set of low resolution detection signals or low resolution data needed for eliminating the falsification in the high resolution detection signals or high resolution data is acquired in the low resolution detection mode. The set of low resolution detection signals is acquired with one single scan covering the complete 2D field of view 170 and therefore all subfields contained in this field. Nevertheless, it is also thinkable to acquire the low resolution detection signals only for the adjacent subfields by conducting an appropriate scan. Such appropriate scan covers for example the field of interest 174 and the subfields immediately surrounding the field of interest 174. The set of high resolution detection signals is acquired with one single scan covering the complete field of interest 174 and therefore all subfields of interest contained in this field.

The set of high resolution detection signals comprises a number of subsets of high resolution detection signals, each subset being assigned to an individual subfield of interest. The set of low resolution detection signals comprises a number of subsets of low resolution detection signals. As the low resolution detection signals are acquired with a scan covering the complete 2D field of view 170, the set of low resolution detection signals comprises a subset of low resolution detection signals for each subfield. Thus, for an arbitrary specific subfield of interest the set of low resolution detection signals contains in any case the subset of low resolution detection signals being assigned to the corresponding adjacent subfields being adjacent to the specific subfield of interest.

The reconstruction unit 152 is adapted for reconstructing an individual particle distribution quantity for a specific subfield of interest depending on that subset of high resolution detection signals being assigned to the specific subfield of interest and that subsets of low resolution detection signals being assigned to those adjacent subfields being adjacent to the specific subfield of interest. Consequently, the particle distribution quantity is compound of a number of individual particle distribution quantities. Assuming subfield of interest E4 is the specific subfield, for determining the individual particle distribution quantity for this specific subfield, the subset of high resolution detection signals acquired for the specific subfield E4 and the subsets of low resolution detection signals acquired for the adjacent subfields D3, D4, D5, E3, E5, F3, F4 and F5 are taken into account. Hence, for determining the individual particle distribution quantity the orthogonal adjacent subfields and the diagonal adjacent subfields are taken into account. Alternatively it is conceivable only to take the orthogonal adjacent subfields into account. With this measure the time required for reconstructing the particle distribution quantity would be less. In this case, in the foregoing example only the adjacent subfields D4, E3, E5 and F4 would be considered.

As explained above, the particle distribution quantity is determined depending on a set of high resolution detection signals and a set of low resolution detection signals. Even in case the set of low resolution detection signals does not contain for all subfields of interest an assigned subset of low resolution detection signals this approach results in a suitable result—indeed, in case for none of the subfields of interest an assigned subset of low resolution detection signals exists and therefore solely subsets of low resolution signals exist being assigned to subfields surrounding the field of interest. Based on FIG. 6, subfields surrounding the field of interest 174 are at least the subfields B1, B2, B3, B4, B5, B6, C1, C6, D1, D6, E1, E6, F1, F2, F3, F4, F5 and F6. Of course, any other subfield not contained in the field of interest 174 is a surrounding subfield.

In case of missing subsets of low resolution detection signals the particle distribution quantity is reconstructed using an iterative approach. This iterative approach is explained below for a constellation having two subfields of interest. This shall have not have any restricting impact. Of course, the iterative approach can be applied to constellations having an arbitrary number of subfields of interest.

In a first iterative step, for one of the two subfields of interest the individual particle distribution quantity is reconstructed under the assumption that the spatial distribution of the magnetic particles within the other subfield of interest is zero. This reconstructed individual particle distribution quantity is an approximation for the subset of low resolution detection signals assigned to the one subfield of interest. In a second iterative step, this reconstructed individual particle distribution quantity is used for reconstructing the individual particle distribution quantity for the other subfield of interest. This reconstructed individual particle distribution quantity is an approximation for the subset of low resolution detection signals assigned to the other subfield of interest. This reconstructed individual particle distribution quantity is used for reconstructing a further individual particle distribution quantity for the one subfield. Iterating this several times results in a particle distribution quantity of high quality.

At this point the multi-station approach and the other approach for scanning subfields shall be explained. For this purpose, acquiring the low resolution detection signals with a scan covering the complete 2D field of view 170 is regarded. This shall not have any restricting impact. The following explanations are also valid for any other arbitrary set of subfields. Conducting a multi-station approach for example six sets of subfields are scanned. Beginning with a first set of subfields containing the subfields A1, A2, A3, B1, B2, B3, C1, C2, C3, followed by a second set of subfields containing the subfields D1, D2, D3, E1, E2, E3, F1, F2, F3, followed by a third set of subfields containing the subfields G1, G2, G3, H1, H2, H3, I1, I2, I3, followed by a fourth set of subfields containing the subfields A4, A5, A6, B4, B5, B6, C4, C5, C6, followed by a fifth set of subfields containing the subfields D4, D5, D6, E4, E5, E6, F4, F5, F6, followed by a sixth set of subfields containing the subfields G4, G5, G6, H4, H5, H6, I4, I5, I6. Whereas, with the approach according to which the first sub-zone is continuously moved from one subfield to another, the subfields are for example scanned in the following order: A1, A2, A3, A4, A5, A6, B6, B5, B4, B3, B2, B1, C1, C2, C3, C4, C5, C6, D6, D5, ... I6.

Because of the illustration in FIG. 6 the explanations above relating to the 2D field of view 170, the field of interest 174 and the object of interest 172 are made with regard to 2D structures. However, these explanations are accordingly valid for 3D fields and objects. With regard to a three-dimensional field of view an orthogonal adjacent subfield has a surface in common with the specific subfield of interest, whereas a diagonal adjacent subfield solely has an edged in common with the specific subfield of interest.

The subfields being identified as subfields of interest form a field of interest. However, the subfields of interest contained within the field of interest are at the same time adjacent subfields. For example, with regard to the specific subfield of interest E4 the subfields of interest D3, D4, D5, E3 and E5 are adjacent subfields.

Advantageously, only subfields being arranged adjacent to a specific subfield of interest and covering at least a portion of the object of interest or at least a portion of the further object are identified as adjacent subfields. This measure results in a time saving reconstruction of the particle distribution quantity. However, this shall not have any restricting impact on the invention. Of course, any subfield being arranged adjacent to a specific subfield of interest can be identified as an adjacent subfield regardless of whether this adjacent subfield covers a portion of the object of interest or a portion of the further object or not.

Furthermore, not only subfields being arranged in the immediate vicinity of a specific subfield of interest can be identified as adjacent subfields but also subfields being arranged further away from the specific subfield of interest but covering at least a portion of a further object. For example, with regard to the specific subfield of interest E4 additionally the subfields G3, G4 and G5 can be identified as adjacent subfields. The same applies to subfields of interest being arranged further away from a specific subfield of interest. For example, with regard to the specific subfield of interest E4 the subfield of interest C4 can be identified as adjacent subfield. Considering adjacent subfields being arranged further away from a specific subfield of interest, results in a particle distribution quantity of high quality.

Figure 7:
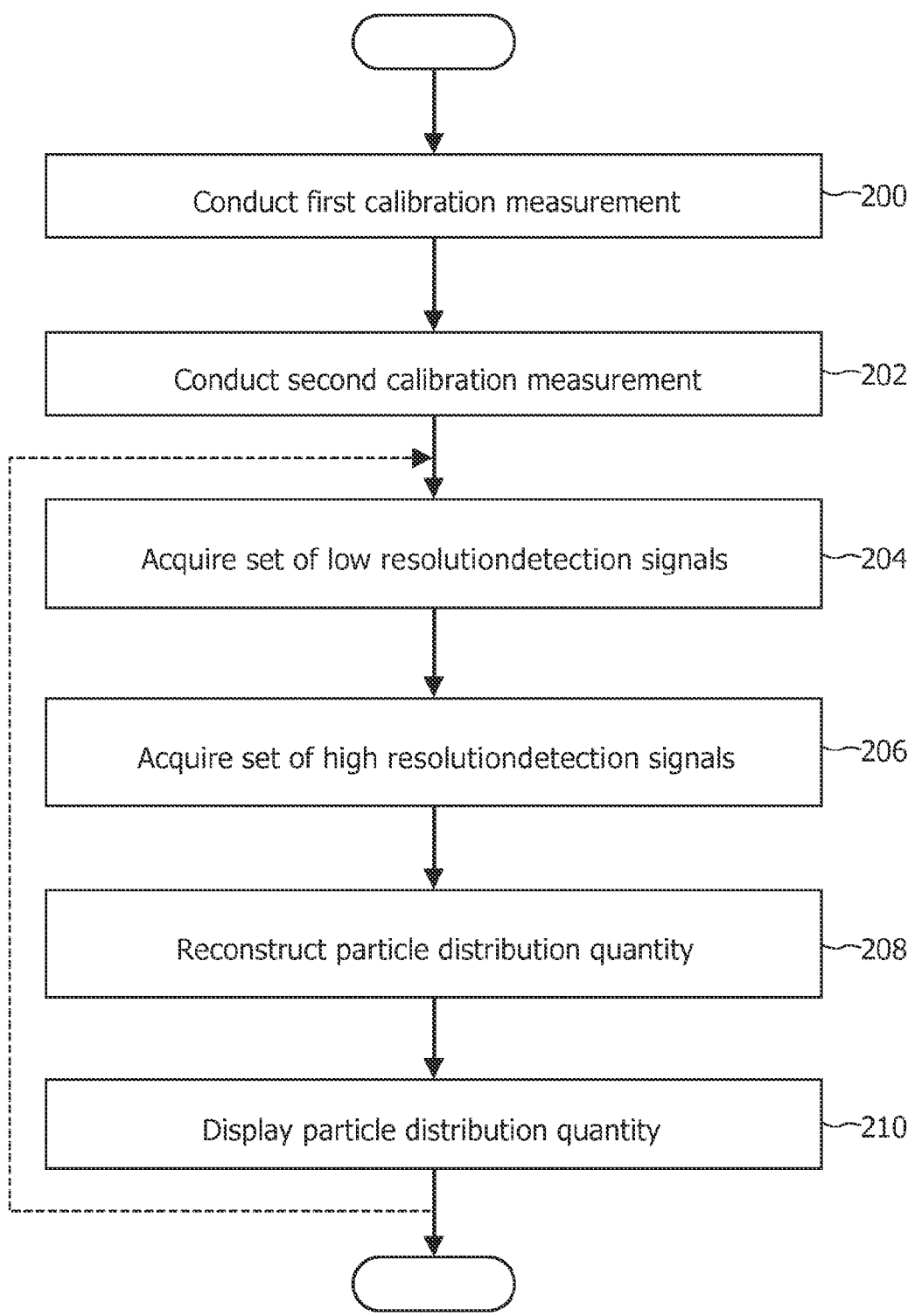
FIG. 7 shows a flow chart of an MPI method according to the present invention.

FIG. 7 shows a flowchart of an embodiment of the method according to the present invention. In a step 200 a first calibration measurement for determining a first system function for the low resolution detection mode is conducted. The corresponding first set of system data is stored in the storage unit 162. In a step 202 a second calibration measurement for determining a second system function for the high resolution detection mode is conducted. The corresponding second set of system data is stored in the storage unit 162, too.

In a step 204 a set of low resolution detection signals is acquired with one single scan covering the complete field of view 28 and therefore all subfields contained in this field. For this purpose the field of view 28 is subdivided into a number of planes like illustrated in FIG. 6. The number of planes is scanned as explained in connection with FIG. 6. The acquired set of low resolution detection signals can be used for positioning the object to be examined and for planning the filed of interest 174. This can be done automatically or based on inputs given by the operator of the apparatus 100.

In a step 206 a set of high resolution detection signals is acquired with one single scan covering the complete field of interest 174. The filed of interest 174 is also subdivided in a number of planes and the approach for scanning as explained in connection with scanning the field of view 28 can be used accordingly. According to the illustration in FIG. 7, first the set of low resolution detection signals and subsequently the set of high resolution detection signals are acquired. This shall not have any restricting impact on the invention. Of course, the control unit 150 can be adapted for controlling the drive field signal generator unit 130 and the receiving unit 140 for acquiring the set of low resolution detection signals and the set of high resolution detection signals in an interleaved manner.

In a step 208 a particle distribution quantity is reconstructed depending on the set of high resolution detection signals and the set of low resolution detection signals. For this purpose the following approach starting with $$S_H = G_H \cdot C^*_H \quad (1)$$

is used. In equation (1) $S_H$ represents the acquired high resolution detection signals, $G_H$ represents the system function for the high resolution detection mode and $C^*_H$ is the unknown particle distribution quantity representing the spatial distribution of the magnetic particles within the object of interest 172, wherein $C^*_H$ is falsified by low frequency contributions originating from adjacent subfields. $S_H$ comprises a number of subsets of high resolution detection signals, each subset being assigned to an individual subfield of interest. This shall have no restricting impact on the invention. Of course, $S_H$ can comprises as many subsets as subfields contained in the field of view exist. In an appropriate manner $C^*_H$ comprises individual particle distribution quantities being assigned to individual subfields. These explanations are also valid for corresponding variables or quantities used below.

Equation (1) can be rewritten as follows:

$$S_H = G_H \cdot C_H + G_N \cdot C_N. \tag{2}$$

$C_H$ is the unknown particle distribution quantity representing the spatial distribution of the magnetic particles within the object of interest 172, wherein falsifications arising from low frequency contributions being originated from adjacent subfields are eliminated. $C_N$ represents the amount in the particle distribution quantity $C^*_H$ caused by said low frequency contributions. As $C_N$ represents the spatial distribution of the magnetic particles at low frequencies a system function for the low resolution detection mode represented by $G_N$ is used. The system function $G_N$ represents the low resolution concentration information from the areas adjacent to an area for which a particle distribution quantity shall be reconstructed.

The unknown particle distribution quantity $C_H$ can be determined by solving the following equation using for example Tikhonov regularization:

$$\|S_H - G_H \cdot C_H - G_N \cdot C_N\| \stackrel{!}{=} \min \tag{3}$$

However, the term $G_N C_N$ is still unknown. This unknown term can be determined by conducting a low resolution scan for determining a set of low resolution detection signals. According to equation (1) the following approach can be used:

$$S_N = G_N \cdot C^*_N, \tag{4}$$

wherein $S_N$ represents the acquired low resolution detection signals and $C^*_N$ is the unknown particle distribution quantity representing the spatial distribution of the magnetic particles within the object of interest 172. $C^*_N$ is also falsified by contributions originating from adjacent subfields.

In principle, the unknown particle distribution quantity $C^*_N$ can be determined by solving the following equation using for example Tikhonov regularization:

$$\|S_N - G_N \cdot C^*_N\| \stackrel{!}{=} \min \tag{5}$$

However, for determining $C_H$ using equation (3) not the falsified particle distribution quantity $C^*_N$ but a particle distribution quantity $C_N$ for which the falsifications are eliminated is needed. As no further set of detection signals is available for eliminating the falsifications contained in $S_N$ reconstructing a particle distribution quantity using equation (5) is done iteratively resulting in a corrected particle distribution quantity $\tilde{C}^*_N$ for which the falsifications are best possible eliminated. This corrected particle distribution quantity is a suitable approximation for $C_N$. Reconstructing a particle distribution quantity means reconstructing individual particle distribution quantities for single specific subfields, wherein the particle distribution quantity is compound of the individual particle distribution quantities. Therefore, for the subfields contained in the field of view, particularly for all subfields of the field of view, an individual particle distribution quantity is reconstructed iteratively.

In a first iterative step it is assumed that the spatial distribution of the magnetic particles in adjacent subfields being adjacent to a respective subfield for which the individual particle distribution quantity shall be reconstructed is zero. Therefore, the specific subsets of low resolution detection signals contained in $S_N$ and being assigned to the adjacent subfields are set to zero. The result of the first iterative step is an approximated individual particle distribution quantity. The approximated individual particle distribution quantities are compound to a first corrected particle distribution quantity $\tilde{C}^*_{N1}$. This first corrected particle distribution quantity can be used as a corrected set of low resolution detection signals being the basis for a second iterative step. Further iterative steps may follow. Using an appropriate curve fitting method the iterative reconstruction of the particle distribution quantity is stopped by the time a claimed quality for the corrected particle distribution quantity is achieved. Finally, the result is a corrected particle distribution quantity $\tilde{C}^*_{N1}$. Using this corrected particle distribution quantity a corrected set of low resolution detection signals can be determined according to $$\tilde{S}_N = G_N \cdot \tilde{C}^*_{N1}. \tag{6}$$

Using equation (6) equation (3) can be written as $$\|S_H - \tilde{S}_N - G_H \cdot C_H\| \stackrel{!}{=} \min. \tag{7}$$

Equation (7) can be solved using for example Tikhonov regularization resulting in $C_H$.

Although the foregoing iterative approach is explained for a situation in which low resolution detection signals are present for adjoining subfields, this approach can also be applied in an appropriate manner to a situation in which high resolution detection signals are present for adjoining subfields.

In an alternative approach, equation (4) can be inserted into equation (3) resulting in $$\|S_H - S_N - G_H \cdot C_H\| \stackrel{!}{=} \min. \tag{8}$$

Solving equation (8) using for example Tikhonov regularization results in a particle distribution quantity that has for the reasons described above not that quality as a particle distribution quantity being determined using equation (7).

The approaches based on equations (1) to (8) are mainly explained with a view to the set of low resolution detection signals, the set of high resolution detection signals and the particle distribution quantity. This shall not have any restricting impact. As both sets of detection signals comprise in each case subsets of detection signals and as the particle distribution quantity is compound of a number of individual particle distribution quantities, these explanations are accordingly valid for said subsets of detection signals and said individual particle distribution quantities, too.

In a step 210 the reconstructed particle distribution quantity is displayed.

It may also be feasible to obtain the set of low resolution detection signals by solely applying focus fields.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

Any reference signs in the claims should not be construed as limiting the scope.

The invention claimed is:

1. An apparatus (100) for influencing and/or detecting magnetic particles in a field of view (28), wherein the field of view (28) comprises at least one subfield of interest covering at least a portion of an object of interest, wherein the object of interest contains magnetic particles, and wherein the apparatus has at least two different detection modes, encompassing a high resolution detection mode and a low resolution detection mode, which apparatus comprises:

selection means comprising a selection field signal generator unit (110) and selection field elements (116) for generating a magnetic selection field (50) having a pattern in space of a magnetic field strength such that a first sub-zone (52) having a low magnetic field strength and a second sub-zone (54) having a higher magnetic field strength are formed in the field of view (28), wherein in the first sub-zone (52) the magnetization of the magnetic particles is not saturated and wherein in the second sub-zone (54) the magnetization of the magnetic particles is saturated;

drive means comprising a drive field signal generator unit (130) and drive field coils (136a, 136b, 136c) for changing the position in space of at least the first sub-zone (52) in the field of view (28) by means of a magnetic drive field so that a magnetization of the magnetic particles contained in said object of interest changes locally;

receiving means comprising at least one signal receiving unit (140) and at least one receiving coil (148) for acquiring detection signals, which detection signals depend on the magnetization in at least a portion of the field of view (28), which magnetization is influenced by the change in the position in space of the at least first sub-zone (52);

a control unit (150) for controlling the signal receiving unit (140) according to the detection mode, wherein in the high resolution detection mode acquires a set of high resolution detection signals and in the low resolution detection mode acquires a set of low resolution detection signals, wherein the set of high resolution detection signals depends on the magnetization of at least one subfield of interest and the set of low resolution detection signals depends on the magnetization of at least one adjacent subfield being arranged adjacent to the at least one subfield of interest; and a reconstruction unit (152) for reconstructing a particle distribution quantity characterizing a spatial distribution of the magnetic particles within at least a portion of the object of interest, wherein the particle distribution quantity is reconstructed depending on the set of high resolution detection signals and the set of low resolution detection signals.

2. An apparatus (100) as claimed in claim 1,
wherein the drive field signal generator unit (130) is adapted for changing the position in space of the first sub-zone (52) along a defined trajectory, wherein the control unit (150) is adapted for controlling the drive field signal generator unit (130) according to the detection mode, and wherein in the high resolution detection mode the position in space changes along a high resolution trajectory and in the low resolution detection mode the position in space changes along a low resolution trajectory.

3. An apparatus (100) as claimed in claim 2,
wherein the defined trajectory has the form of a closed Lissajous curve, wherein a first closed Lissajous curve having a first density of trajectory is used as low resolution trajectory and a second Lissajous curve having a second density of trajectory is used as high resolution trajectory, and wherein the first density of trajectory is lower than the second density of trajectory.

4. An apparatus (100) as claimed in claim 1,
wherein the selection field signal generator unit (110) is adapted for generating a magnetic selection field showing a defined gradient strength, wherein the control unit (150) is adapted for controlling the selection field generator unit (110) according to the detection mode, wherein in the low resolution detection mode a first magnetic selection field showing a first gradient strength is generated and in the high resolution detection mode a second magnetic selection field showing a second gradient strength is generated, and wherein the first gradient strength is smaller than the second gradient strength.

5. An apparatus (100) as claimed in claim 1,
wherein the field of view (28) comprises a number of subfields, wherein the drive field signal generator unit (130) is adapted for changing the position in space of the first sub-zone (52) along a defined trajectory having a spatial extent essentially defining the spatial extent of an individual subfield, and
wherein the apparatus (100) further comprises focus means comprising a focus field signal generator unit (120) and focus field coils (126a, 126b, 126c) for generating a magnetic focus field for focusing the first sub-zone (52) on an arbitrary subfield contained in the number of subfields.

6. An apparatus (100) as claimed in claim 5,
wherein the control unit (150) is adapted for controlling the focus field signal generator unit (120) for continuously moving the first sub-zone (52) from a first subfield to a second subfield.

7. An apparatus (100) as claimed in claim 1,
wherein the field of view (28) comprises a number of subfields, wherein the set of low resolution detection signals depends on the magnetization of all subfields.

8. An apparatus (100) as claimed in claim 1,
wherein the field of view (28) comprises a number of subfields of interest, wherein the set of high resolution detection signals depends on the magnetization of all subfields of interest.

9. An apparatus (100) as claimed in claim 1,
wherein the control unit (150) is adapted for controlling the drive field signal generator unit (130) and the receiving unit (140) for acquiring at first the set of low resolution detection signals and subsequently the set of high resolution detection signals.

10. An apparatus (100) as claimed in claim 1,
wherein the field of view (28) comprises a number of subfields, and wherein the reconstruction unit (152) comprises a subfield identification unit (160) for identifying at least one subfield of interest and/or for identifying at least one adjacent subfield each comprised in the field of interest (28).

11. An apparatus (100) as claimed in claim 1,
wherein the control unit (150) is adapted for controlling the drive field signal generator unit (130) and the receiving unit (140) for acquiring the set of low resolution detection signals and the set of high resolution detection signals in an interleaved manner.

12. An apparatus (100) as claimed in claim 1,
wherein the set of high resolution detection signals comprises a number of subsets of high resolution detection signals, each subset being assigned to an individual subfield of interest,
wherein the set of low resolution detection signals comprises a number of subsets of low resolution detection signals, each subset being assigned to an individual adjacent subfield,
wherein the reconstruction unit (150) is adapted for reconstructing an individual particle distribution quantity for a specific subfield of interest,
wherein the individual particle distribution quantity depends on that subset of high resolution detection signals being assigned to the specific subfield of interest and that subsets of low resolution detection signals being assigned to that adjacent subfields being adjacent to the specific subfield of interest.

13. An apparatus (100) as claimed in claim 1,
wherein the apparatus (100) further comprises a storage unit (162) for storing a first set of system data characterizing the apparatus' low resolution system function and a second set of system data characterizing the apparatus' high resolution system function.

14. A method for influencing and/or detecting magnetic particles in a field of view (28), wherein the field of view (28) comprises at least one subfield of interest covering at least a portion of an object of interest, wherein the object of interest contains magnetic particles, wherein the magnetic particles can be detected in a high resolution detection mode and in a low resolution detection mode, which method comprises the steps of:
  generating a magnetic selection field (50) having a pattern in space of a magnetic field strength such that a first sub-zone (52) having a low magnetic field strength and a second sub-zone (54) having a higher magnetic field strength are formed in the field of view (28), wherein in the first sub-zone (52) the magnetization of the magnetic particles is not saturated and wherein in the second sub-zone (54) the magnetization of the magnetic particles is saturated;
  changing the position in space of at least the first sub-zone (52) in the field of view (28) by means of a magnetic drive field so that a magnetization of the magnetic particles contained in said object of interest changes locally;
  acquiring detection signals, which detection signals depend on the magnetization in at least a portion of the field of view (28), which magnetization is influenced by the change in the position in space of the at least first sub-zone (52);
  controlling the acquiring of a set of high resolution detection signals in the high resolution detection mode, wherein the set of high resolution detection signals depends on the magnetization of at least one subfield of interest;
  controlling the acquiring of a set of low resolution detection signals in the low resolution detection mode, wherein the set of low resolution detection signals depends on the magnetization of at least one adjacent subfield being arranged adjacent to the at least one subfield of interest; and
  reconstructing a particle distribution quantity characterizing a spatial distribution of the magnetic particles within at least a portion of the object of interest, wherein the particle distribution quantity is reconstructed depending on the set of high resolution detection signals and the set of low resolution detection signals.

15. A non-transitory computer readable medium containing a computer program comprising program code for causing a computer to control an apparatus to influence and/or detect magnetic particles in a field of view, wherein the field of view comprises at least one subfield of interest covering at least a portion of an object of interest, wherein the object of interest contains magnetic particles, wherein the magnetic particles can be detected in a high resolution detection mode and in a low resolution detection mode wherein said computer program is executable by the computer to cause executing of steps of:
  generating a magnetic selection field (50) having a pattern in space of a magnetic field strength such that a first sub-zone (52) having a low magnetic field strength and a second sub-zone (54) having a higher magnetic field strength are formed in the field of view (28), wherein in the first sub-zone (52) the magnetization of the magnetic particles is not saturated and wherein in the second sub-zone (54) the magnetization of the magnetic particles is saturated;
  changing the position in space of at least the first sub-zone (52) in the field of view (28) by means of a magnetic drive field so that a magnetization of the magnetic particles contained in said object of interest changes locally;
  acquiring detection signals, which detection signals depend on the magnetization in at least a portion of the field of view (28), which magnetization is influenced by the change in the position in space of the at least first sub-zone (52);
  controlling the acquiring of a set of high resolution detection signals in the high resolution detection mode, wherein the set of high resolution detection signals depends on the magnetization of at least one subfield of interest;
  controlling the acquiring of a set of low resolution detection signals in the low resolution detection mode, wherein the set of low resolution detection signals depends on the magnetization of at least one adjacent subfield being arranged adjacent to the at least one subfield of interest; and
  reconstructing a particle distribution quantity characterizing a spatial distribution of the magnetic particles within at least a portion of the object of interest, wherein the particle distribution quantity is reconstructed depending on the set of high resolution detection signals and the set of low resolution detection signals.

* * * * *